United States Patent
Orwar et al.

(10) Patent No.: US 11,234,963 B2
(45) Date of Patent: *Feb. 1, 2022

(54) PHARMACEUTICAL COMBINATION FOR THE TREATMENT OF CANCER

(71) Applicant: Piramal Enterprises Limited, Mumbai (IN)

(72) Inventors: Owe Orwar, Hovas (SE); Sreesha Srinivasa, Bangalore (IN); Prabha Mishra, Thane (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/725,601

(22) Filed: Dec. 23, 2019

(65) Prior Publication Data

US 2020/0138782 A1     May 7, 2020

Related U.S. Application Data

(63) Continuation of application No. 15/313,543, filed as application No. PCT/IB2015/053963 on May 27, 2015, now Pat. No. 10,555,931.

(60) Provisional application No. 62/003,575, filed on May 28, 2014.

(51) Int. Cl.

| | |
|---|---|
| *A61K 31/4025* | (2006.01) |
| *A61K 45/06* | (2006.01) |
| *A61K 31/41* | (2006.01) |
| *A61K 31/7135* | (2006.01) |
| *A61K 31/513* | (2006.01) |
| *A61K 31/519* | (2006.01) |
| *A61K 31/553* | (2006.01) |
| *A61K 33/36* | (2006.01) |

(52) U.S. Cl.
CPC .......... *A61K 31/4025* (2013.01); *A61K 31/41* (2013.01); *A61K 31/513* (2013.01); *A61K 31/519* (2013.01); *A61K 31/553* (2013.01); *A61K 31/7135* (2013.01); *A61K 33/36* (2013.01); *A61K 45/06* (2013.01)

(58) Field of Classification Search
CPC ...... A61K 31/41; A61K 45/06; A61K 31/519; A61K 31/7135; A61K 31/513; A61K 31/4025; A61K 33/36; A61K 31/553; A61K 2300/00; A61P 35/00
See application file for complete search history.

(56) References Cited

U.S. PATENT DOCUMENTS

| | | | | |
|---|---|---|---|---|
| 2011/0104308 A1* | 5/2011 | Stamler | ................. | A61K 31/65 424/708 |
| 2012/0165406 A1* | 6/2012 | Arbiser | ................. | A61P 11/06 514/548 |

FOREIGN PATENT DOCUMENTS

| | | |
|---|---|---|
| WO | 2008057402 A2 | 5/2008 |
| WO | 2009076170 A2 | 6/2009 |
| WO | 2009137378 A2 | 11/2009 |
| WO | 2010129858 A1 | 11/2010 |
| WO | 2012123889 A1 | 9/2012 |
| WO | 2012125510 A1 | 9/2012 |
| WO | 2012164497 A1 | 12/2012 |

OTHER PUBLICATIONS

CN 101513528 A, Eng. Abstract, 2009.*
Liu et al., "Suppression of TG-Interacting Factor Sensitizes Arsenic Trioxide-Induced Apoptosis in Human Hepatocellular Carcinoma Cells", Biochem. J., vol. 438, pp. 349-358 (2011).
International Search Report for PCT/IB2015/053963 dated Aug. 25, 2015.
Extended European Search Report dated Dec. 6, 2017.
Rathkopf et al., "Phase I Study of Flavopiridol with Oxaliplatin and Florouracil/Leucovorin in Advanced Solid Tumors", Clin Cancer Res, vol. 15, No. 23, pp. 7405-7411(2009).
Pishvaian et al., "Abstract 5047: Synergistic anti-cancer activity of the CDK4/6 inhibitor PD-0332991 in combination with 5-fluorouracil-based chemotherapy in human colon cancer cells", Cancer Research, XP055313469.
Bible et al., "Cytotoxic Synergy between Flavopiridol (NSC 649890, L86-8275) and Various Antineoplastic Agents: The Importance of Sequence of Administration", Cancer Research, vol. 57, pp. 3375-3380 (1997).
Guha, "Cyclin-dependent kinase inhibitors move into Phase III", Nature, vol. 11, pp. 892-894 (2012).
Cicenas, "The CDK inhibitors in cancer research and therapy", J Cancer Res Clin Oncol, vol. 137, pp. 1409-1418 (2011).
Urig et al., "On the potential of thioredoxin reductase inhibitors for cancer therapy," Seminars in Cancer Biology 16 (2006) 452-465, 2006.
Voruciclib, PubChem 2012 cited by the examiner in Non-Final Rejection dated Apr. 2, 2018 in connection with U.S. Appl. No. 15/313,543.
Wei Fu et al. ("The Cyclin-Dependent Kinase Inhibitor SCH 727965 (Dinaclicib) Induces the Apoptosis of Osteosarcoma Cells," in Molecular Cancer Therapeutics, vol. 10, No. 6, Jun. 2011.

* cited by examiner

*Primary Examiner* — Blessing M Fubara
(74) *Attorney, Agent, or Firm* — Morgan, Lewis & Bockius LLP

(57) ABSTRACT

The present invention relates to a pharmaceutical combination comprising a CDK inhibitor and at least one antioxidant enzyme inhibitor for use in the treatment of cancer. The present invention also relates to a method for the treatment of cancer comprising administering to a subject in need thereof, a therapeutically effective amount of a CDK inhibitor and a therapeutically effective amount of at least one antioxidant enzyme inhibitor. The pharmaceutical combination of the present invention exhibits synergistic effect when used in the treatment of cancer.

17 Claims, 11 Drawing Sheets

14A

14B

14C

PHARMACEUTICAL COMBINATION FOR THE TREATMENT OF CANCER

CROSS-REFERENCE TO RELATED APPLICATIONS

This application is a continuation of U.S. patent application Ser. No. 15/313,543, filed Nov. 22, 2016, which is a U.S. National Stage Patent Application of International Patent Application No. PCT/IB2015/053963, filed May 27, 2015, which claims the benefit of U.S. Provisional Patent Application No. 62/003,575, filed May 28, 2014, all of which are incorporated by reference herein in their entireties.

FIELD OF THE INVENTION

The present invention relates to a pharmaceutical combination comprising a CDK inhibitor and at least one antioxidant enzyme inhibitor for use in the treatment of cancer. The present invention also relates to a method for the treatment of cancer comprising administering to a subject in need thereof, a CDK inhibitor in combination with at least one antioxidant enzyme inhibitor.

BACKGROUND OF THE INVENTION

Cancer is a disease characterized by the unusual control of cell growth or uncontrolled cell division. The uncontrollable cell division is an effect of a break down in the natural life cycle of cells. There are over 100 different types of cancers, which are classified by the type of cells initially affected such as bladder cancer, breast cancer, colon cancer, rectal cancer, endometrial cancer, kidney (renal cell) cancer, leukemia, small cell lung cancer, non-small cell lung cancer, pancreatic cancer, prostate cancer, thyroid cancer, skin cancer, non-Hodgkin's lymphoma, melanoma and head and neck cancer.

Cancer is a leading cause of death worldwide. It causes 1 in 8 deaths worldwide and is rapidly becoming a global pandemic. According to World Cancer Research Fund International, the cancer statistics worldwide based on GLOBOCAN 2012, there were an estimated 14.1 million cancer cases around the world in 2012, of these 7.4 million cases were in men and 6.7 million in women. This number is expected to increase to 24 million by 2035.

There are many chemotherapeutic treatments available for cancer patients, but taking into consideration the worldwide statistics of the cancer patients and pandemic of the disease there is a continuous need to develop new chemotherapeutic regimens for the treatment of cancer. For instance, cyclin-dependent kinase (CDK) inhibitors are anticancer agents which provide a promise for the treatment of proliferative disorders, particularly cancers. CDK is a family of protein kinases and it plays an essential role in the control of life cycle of cell and/or proliferation. CDK deregulation is one characteristic found in most cancer cells. The mammals have naturally occurring CDK inhibiting proteins, which regulate CDK and in turn regulate life cycle of cell. The CDK deregulation may be due to an overabundance of CDK or may be due to a malfunction of naturally occurring CDK inhibiting proteins. Therefore, CDK inhibition has become an attractive strategy towards recent developments in chemotherapies for cancer. Thus, CDK inhibitors, such as flavopiridol, seliciclib, olomoucine and purvalanol A find use in the treatment of cancers. However, as per the recent developments in cancer research, it is found that current treatment options for cancer include combination therapy. The combination therapy approach is directed to a protocol involving combining different anticancer agents having different biological mechanism. An optimal combination chemotherapy protocol may result in increased therapeutic efficacy, decreased host toxicity, and minimal or delayed drug resistance. Therefore, efforts have been directed to combine known CDK inhibitors with other therapeutic agents to provide an effective cancer therapy. Among other therapeutic agents, particularly chemotherapeutic agents, consideration is given to those agents, which work through the control of proliferation, redox states and apoptosis.

It is known that reactive oxygen species (ROS) are mediators of intracellular signaling cascades. ROS are produced within cells, even under normal physiological conditions, which include free radicals with unpaired electrons, such as the superoxide anion, hydroxyl radical and oxidants such as hydrogen peroxide ($H_2O_2$), all of which are inherently unstable and often highly reactive. In normal physiological conditions of mammal the cellular oxidation-reduction (redox) equilibrium in aerobic cells is maintained by ROS and antioxidants (*Free Radic. Biol. Med.* 2001, 31, 1287-1312). However, under certain conditions the excessive production of ROS may lead to oxidative stress, loss of cell function, and ultimately apoptosis or necrosis. A balance between oxidant and antioxidant intracellular systems is hence vital for cell function, regulation and adaptation to diverse growth conditions. The cancer cells are normally under high oxidative stress and also express high levels of antioxidant proteins. These antioxidant proteins have been shown to be upregulated in hypoxic regions of certain tumors, suggesting that inhibitors could potentially exhibit enhanced hypoxic toxicity and/or indirect anti-angiogenic effect. Also, it is known that cancer cells that are detached from their normal environment, as they would be during metastasis, rely on the activity of antioxidant enzymes to facilitate their survival. The level of antioxidant enzymes is found to be high in certain cancers (tumors). Therefore, while considering treatment of certain cancers, it would be a prudent approach to decrease the levels of the antioxidant enzymes.

Antioxidant enzyme inhibitors are the molecules that regulate ROS production by preventing or reducing the oxidation of ROS targets. Humans have evolved highly complex antioxidant systems, which work synergistically, and in combination with each other to protect the cells and organ systems of the body against damage due to unregulated ROS level. These antioxidants are produced either endogenously or received from exogenous sources. In mammalian cells, the thioredoxin (Trx) and the glutathione systems are two major thiol-dependent antioxidant systems.

Several studies imply that the deregulated Trx expression is one of the enhancers of cancer cell growth, which occurs either through the direct stimulation of cancer cell growth or through the inhibition of cancer cell apoptosis. The Trx system composed of the redox-active protein thioredoxin (Trx), the enzyme thioredoxin reductase (TrxR), and Nicotinamide Adenine Dinucleotide Phosphate (NADPH), which is present in nearly all living cells. The system functions in thiol-dependent thiol-disulfide exchange reactions which are crucial to control of the reduced intracellular redox environment, cellular growth, defense against oxidative stress or control of apoptosis and has multifaceted roles in mammalian cells including implications in cancer. Trx system is a ubiquitous oxidoreductase system with antioxidant and redox regulatory roles. The oxidized form of Trx is reduced by thioredoxin reductase (TrxR). The antioxidant property of Trx functions through directly quenching singlet oxygen and scavenging hydroxyl radicals, or indirectly by reducing oxidized reactive oxygen species target proteins.

Glutathione is the principal intracellular non-protein thiol, which provides primary defense against oxidative stress. The glutathione system includes the reduced glutathione referred to as GSH and an oxidized form of glutathione referred to as GSSG; the enzymes required for its synthesis and recycling, such as gamma-glutamate cysteine ligase (γ-GCL), glutathione synthetase (GS), glutathione reductase (GR/GSR) and gamma glutamyl transpeptidase (γ-GGT); and the enzymes required for its use in metabolism and in mechanisms of defense against ROS induced oxidative stress, such as glutathione s-transferases (GSTs) and glutathione peroxidases (GPxs) (*Cent. Nerv. Syst. Agents Med. Chem.* 2010, 10(4), 287-297). Glutathione is the essential cofactor for many enzymes that require thiol-reducing equivalents, and helps to keep redox-sensitive active sites on enzyme in the necessary reduced state. The higher-order thiol cell systems, the metallothioneins, thioredoxins and other redox regulator proteins are ultimately regulated by GSH levels and the GSH/GSSG redox ratio. The glutathione system is responsible for scavenging ROS and maintaining protein thiols in their appropriate redox state in the cytosol and mitochondrion, which is an important protective mechanism for minimizing oxidative damage.

Expressions of thioredoxin/thioredoxin reductase and glutathione (GSH) are found to be deregulated in many cancer cells and therefore, the cancer cells are normally under high oxidative stress. In fact, unregulated ROS level is linked to many cancers such as bladder cancer, brain tumor, breast cancer, cervical cancer, gastric cancer, liver cancer, lung cancer, melanoma, multiple myeloma, leukemia, lymphoma, oral cancer, ovarian cancer, pancreatic cancer, prostate cancer and sarcoma (*Free Radic. Biol. Med.* 2010, 49(11), 1603-1616). Thus, taking into consideration the significant role of thioredoxin, glutathione and other antioxidant enzymes in cancer cells, antioxidant enzymes are regarded as potential target for the treatment of many cancers. An inhibition of antioxidant enzymes leads to oxidation of antioxidant proteins resulting in cellular conditions with regulation of ROS level, which promotes apoptosis. The present inventors have considered combining the antioxidant enzymes inhibitors with CDK inhibitors for use in the treatment of cancers.

SUMMARY OF THE INVENTION

In one aspect, the present invention relates to a pharmaceutical combination comprising a CDK inhibitor and at least one antioxidant enzyme inhibitor for use in the treatment of cancer.

In an aspect, the present invention relates to a pharmaceutical combination comprising a CDK inhibitor and at least one antioxidant enzyme inhibitor(s) selected from glutathione peroxidase inhibitors, glutathione reductase inhibitors, glutathione transferase inhibitors, gamma-glutamate cysteine ligase inhibitors, glutathione synthetase inhibitors, thioredoxin reductase inhibitors. NADPH oxidase inhibitors, catalase inhibitors, peroxiredoxin inhibitors or superoxide dismutase inhibitors; wherein said combination is used in the treatment of cancer.

In another aspect, the present invention relates to a pharmaceutical combination comprising a CDK inhibitor and at least one thioredoxin reductase inhibitor (TrxR inhibitor) for use in the treatment of cancer.

In another aspect, the present invention relates to a pharmaceutical combination comprising a CDK inhibitor, a TrxR inhibitor and a further antioxidant enzyme inhibitor for use in the treatment of cancer.

In yet another aspect, the present invention relates to a method of treating cancer comprising administering to a subject in need thereof, a therapeutically effective amount of a CDK inhibitor and a therapeutically effective amount of at least one antioxidant enzyme inhibitor.

In yet another aspect, the present invention relates to a method of treating cancer comprising administering to a subject in need thereof, a therapeutically effective amount of a CDK inhibitor and a therapeutically effective amount of at least one TrxR inhibitor.

In yet another aspect, the present invention relates to a method of treating cancer comprising administering to a subject in need thereof, a therapeutically effective amount of a CDK inhibitor, a therapeutically effective amount of the TrxR inhibitor and a therapeutically effective amount of a further antioxidant enzyme inhibitor.

In a further aspect, the present invention relates to use of a CDK inhibitor in combination with at least one antioxidant enzyme inhibitor for the treatment of cancer.

In a still further aspect, the present invention relates to use of a CDK inhibitor in combination with at least one antioxidant enzyme inhibitor; for the manufacture of a medicament for the treatment of cancer.

Other aspect and further scope of applicability of the present invention will become apparent from the detailed description.

DETAILED DESCRIPTION OF THE INVENTION

Figure 1:
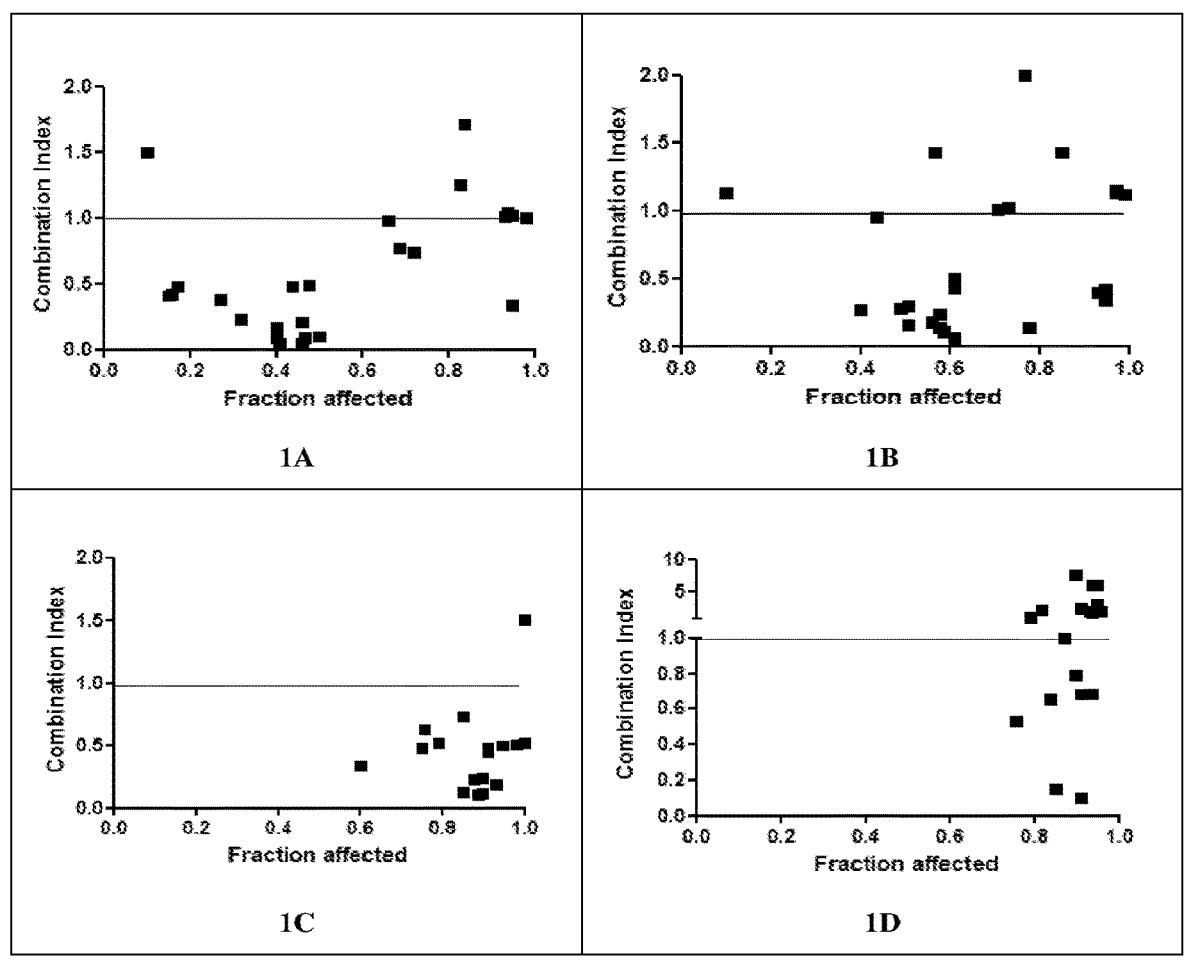
FIG. 1 depicts the effect of the combination of a CDK inhibitor such as voruciclib and an antioxidant enzyme inhibitor such as auranofin at varying concentrations and at different time points in FaDu cell lines, in terms of combination index.

Before the present invention is described in further detail, it is to be understood that the detailed description and specific examples, while indicating embodiments of the invention, are given by way of illustration only, since various changes and modifications within the spirit and scope of the invention will become apparent to those skilled in the art. One skilled in the art, based upon the description herein, can utilize the present invention to its fullest extent. Unless defined otherwise, all technical and specific terms used herein have the same meaning as commonly understood by one of ordinary skill in the art to which the invention belongs.

Definitions

The general terms used hereinbefore and hereinafter preferably have the following meanings within the context of this disclosure, unless otherwise indicated. Thus, the definitions of the general terms as used in the context of the present invention are provided herein below:

The terms "a", "an" and "the" refers to "one or more" when used in the subject specification, including the claims. Thus, for example, reference to "a disease" or "a condition" includes a plurality of diseases or disorders.

It should also be noted that the term "or" is generally employed in its sense including "and/or" unless the content clearly dictates otherwise.

Use of "(s)" as part of a term, includes reference to the term singly or in plurality, e.g. the term therapeutic agent(s) may indicate a single therapeutic agent or two or more therapeutic agents.

As used herein, the term "and/or" refers to at least one or both of the cases which it connects. For example, the term "CDK inhibitor and/or antioxidant enzyme inhibitor" refers to "at least one of CDK inhibitor and antioxidant enzyme inhibitor", which includes the CDK inhibitor alone, antioxidant enzyme inhibitor alone or the combination of the CDK inhibitor and antioxidant enzyme inhibitor.

The term "at least one" refers to one, two, three or more of the therapeutic agents in reference to which the term is used. For example, in the context of the present invention the term "at least one antioxidant enzyme inhibitor" refers to "one or more antioxidant enzyme inhibitors", i.e. one or two or three or more antioxidant enzyme inhibitor(s), which can be used in combination with the CDK inhibitor in the treatment of cancer.

The term "CDK inhibitor" as used herein refers to an agent that is capable of inhibiting one or more cyclin dependent kinase(s) (CDK). CDKs are a family of enzymes which become activated in specific phases of the cell cycle. CDKs consist of a catalytic subunit (the actual cyclin-dependent kinase or CDK) and a regulatory subunit (cyclin). There are at least nine CDKs for example, CDK1, CDK2, CDK3, CDK4, CDK5, CDK6, CDK7, CDK8, CDK9 and at least 15 different types of cyclins for example, cyclin A, B1, B2, D1, D2, D3, E, H. Each step of the cell cycle is regulated by CDK complexes such as: G1/S transition (CDK2/cyclin A, CDK4/cyclin D1-D3, CDK6/cyclin D3), S phase (CDK2/cyclin A), G2 phase 30 (CDK1/cyclin A), G2/M transition phase (CDK1/cyclin B). Aberrant expression and overexpression of these kinases are evidenced in many disease conditions such as cancer.

The term "antioxidant enzyme inhibitor" as used herein refers to an agent that is capable of inhibiting an antioxidant enzyme. Antioxidant enzymes refer to complex molecules present in plants and animals including humans, which inhibit the oxidation of other molecules and thereby reducing or terminating the production of free radicals, by being oxidized themselves, i.e. the antioxidant enzymes are reducing agents which include, but not limited to, glutathione peroxidase, glutathione reductase, glutathione transferase, thioredoxin reductase, NADPH oxidase, catalase, peroxiredoxin or superoxide dismutase. Insufficient levels of antioxidants, or inhibition of the antioxidant enzymes, cause oxidative stress and may damage or kill cells, which plays a significant role in many diseases, including cancers.

The term "pharmaceutical combination" or "combination" as used herein means the combined administration of the therapeutic agents, which can be anticancer agents and/or the agents that potentiate effect of the anticancer agents. In the context of the present invention, the therapeutic agents include a CDK inhibitor and an antioxidant enzyme inhibitor that can be administered independently at the same time or separately within time intervals such that these time intervals allow the combination partners to exhibit a synergistic effect.

The term "synergistic" or "synergistic effect" as used herein refers to the therapeutic effect achieved with the combination of the present invention and/or through the method of treating cancer of this invention; which is greater than the sum of the effects that result from using the CDK inhibitor and the antioxidant enzyme inhibitor(s) alone or separately. Advantageously, such synergy between the therapeutic agents allows for the use of smaller doses of one or both therapeutic agents, provides greater efficacy at the same doses, and/or prevents or delays building up of drug resistance. The combination index (CI) method of Chou and Talalay can be used to determine the synergy, additive or antagonism effect of the therapeutic agents used in the combination (*Cancer Res.*, 2010, 70, 440). When the CI value is less than 1, there is synergy between the agents used in the combination; when the CI value is equal to 1, there is an additive effect between the agents used in the combination and when CI value is more than 1, there is an antagonistic effect between the agents. The synergistic effect can be achieved either by co-formulating the therapeutic agents contained in the pharmaceutical combination or the composition as described herein or administering the said therapeutic agents simultaneously through a unit dosage form or as separate formulations administered simultaneously or sequentially.

The term "therapeutically effective amount" as used herein means an amount of the CDK inhibitor or that of the antioxidant enzyme inhibitor effective in producing the desired therapeutic response in a particular patient (subject) suffering from cancer. Particularly, the term "therapeutically effective amount" includes the amount of the therapeutic agents, which when administered will achieve the desired therapeutic effects. In the context of the present invention the desired therapeutic effects includes partial or total inhibition, delay or prevention of the progression of cancer including cancer metastasis; inhibition, delay or prevention of the recurrence of cancer including cancer metastasis; and/or the prevention of the onset or development of cancer (chemoprevention) in a subject. In respect of the therapeutic amount of the therapeutic agents i.e. the CDK inhibitor and the antioxidant enzyme inhibitor(s), consideration is also given that the amount of each of the therapeutic agent used for the treatment of a subject is low enough to avoid undesired or severe side effects, within the scope of sound medical judgment. The therapeutically effective amount of each of the CDK inhibitor and the antioxidant enzyme inhibitor(s) when used in combination will vary with the age and physical condition of the end user, the severity of cancer, the duration of the treatment, the nature of any other concurrent therapy, the specific type of therapeutic agent employed for the treatment, the particular pharmaceutically acceptable carrier utilized in the pharmaceutical compositions containing the therapeutic agents (the CDK inhibitor and/or the antioxidant enzyme inhibitor(s)) and other relevant factors.

The term "subject" as used herein refers to an animal, particularly a mammal, and more particularly, a human. The term "mammal" used herein refers to warm-blooded vertebrate animals of the class "Mammalia", including humans, characterized by covering of hair on the skin and, in the female, milk-producing mammary glands for nourishing the young. The term mammal includes animals such as cat, dog, rabbit, bear, fox, wolf, monkey, deer, mouse, pig and the human. The term "subject" may be used interchangeably with the term patient. In the context of the present invention the phrase "a subject in need thereof" means a subject in need of the treatment for cancer. Alternatively, the phrase "a subject in need thereof" means a subject (patient) diagnosed with cancer.

The terms "treat," "treatment" or "treated" refer to therapeutic treatment and prophylactic measures to prevent recurrence, wherein the objective is to inhibit or slow down (lessen) an undesired physiological change or disorder, such as the development or spread of cancer. For purpose of this invention desired therapeutic effects include with reference to cancer in a subject include: (i) partial or total inhibition, delay or prevention of the progression of cancer including cancer metastasis; (ii) inhibition, delay or prevention of the recurrence of cancer including cancer metastasis; (iii) the prevention of the onset or development of cancer (chemoprevention) in a subject (iv) inhibition of tumor cell infiltration into peripheral organs; (v) amelioration of cancer, i.e. reducing the severity of the symptoms associated with cancer and/or (vi) relief, to some extent, of one or more symptoms associated with cancer.

The term "apoptosis" refers to the natural process of programmed cell death. It is a process of self-destruction, in which the cell uses specialized cellular machinery to kill itself. The cells disintegrate into membrane-bound particles that are then eliminated by phagocytosis. Apoptosis is a mechanism that enables metazoans to control cell number and eliminate cells that threaten the animal's survival.

The term "pharmaceutically acceptable" as used herein means the carrier, diluent, excipient, and/or salt used in the composition should be compatible with the other ingredients of the formulation, and not deleterious to the recipient thereof. "Pharmaceutically acceptable" also means that the compositions or dosage forms are within the scope of sound medical judgment, suitable for use for a subject such as an animal or human without excessive toxicity, irritation, allergic response, or other problems or complication, commensurate with a reasonable benefit/risk ratio.

The term "therapeutic agent(s)" as used means "an anticancer agent" and/or "an agent that potentiates the effect of the therapeutic agent that is used in combination". The anticancer agent(s) acts by inhibiting or preventing the growth of tumor. The term "anticancer agent" in general refers to the compounds which prevent the cancer cells from multiplying (i.e. anti-proliferative agents). In general, the anticancer agent(s) can be cytotoxic agents or cytostatic agents. Cytotoxic agents prevent cancer cells from multiplying by: (1) interfering with the cell's ability to replicate DNA; and (2) inducing cell death and/or apoptosis in the cancer cells. The cytostatic agents act via modulating, interfering or inhibiting the processes of cellular signal transduction which regulate cell proliferation.

According to one aspect, the present invention relates to a pharmaceutical combination comprising a CDK inhibitor and at least one antioxidant enzyme inhibitor for use in the treatment of cancer.

In an aspect, the present invention relates to a pharmaceutical combination comprising a CDK inhibitor and at least one antioxidant enzyme inhibitor(s) selected from glutathione peroxidase inhibitors, glutathione reductase inhibitors, glutathione transferase inhibitors, gamma-glutamate cysteine ligase inhibitors, glutathione synthetase inhibitors, thioredoxin reductase inhibitors. NADPH oxidase inhibitors, catalase inhibitors, peroxiredoxin inhibitors or superoxide dismutase inhibitors; wherein said combination is used in the treatment of cancer.

In another aspect, the present invention relates to a pharmaceutical combination comprising a CDK inhibitor and at least one thioredoxin reductase inhibitor (TrxR inhibitor) for use in the treatment of cancer.

In another aspect, the present invention relates to a pharmaceutical combination comprising a CDK inhibitor, a TrxR inhibitor and a further antioxidant enzyme inhibitor for use in the treatment of cancer.

In yet another aspect, the present invention relates to a method of treating cancer comprising administering to a subject in need thereof, a therapeutically effective amount of a CDK inhibitor and a therapeutically effective amount of at least one antioxidant enzyme inhibitor.

In yet another aspect, the present invention relates to a method of treating cancer comprising administering to a subject in need thereof, a therapeutically effective amount of a CDK inhibitor and a therapeutically effective amount of at least one TrxR inhibitor.

In yet another aspect, the present invention relates to a method of treating cancer comprising administering to a subject in need thereof, a therapeutically effective amount of a CDK inhibitor, a therapeutically effective amount of the TrxR inhibitor and a therapeutically effective amount of a further antioxidant enzyme inhibitor.

In a further aspect, the present invention relates to use of a CDK inhibitor in combination with at least one antioxidant enzyme inhibitor for the treatment of cancer.

In a further aspect, the present invention relates to use of a CDK inhibitor in combination with at least one antioxidant enzyme inhibitor; for the manufacture of a medicament for the treatment of cancer.

In a still further aspect, the present invention relates to a pharmaceutical kit comprising a container containing: (i) a CDK inhibitor, (ii) one or two or more antioxidant enzyme inhibitor(s) (iii) a package insert comprising instructions for using CDK inhibitor(s) in combination with the antioxidant enzyme inhibitor(s) for the treatment of cancer.

As is indicated herein above, "at least one antioxidant enzyme inhibitor" refers to "one or more antioxidant enzyme inhibitors", i.e. one or two or three or more antioxidant enzyme inhibitor(s), which can be used in combination with the CDK inhibitors in the treatment of cancer.

In an embodiment, the CDK inhibitor is selected from: palbociclib (PD-0332991, Pfizer), dinaciclib (SCH 727965, Merck & Co.), seliciclib (CYC-202, Cyclacel), milciclib (PHA-848125, Pfizer), LEE-011 (Novartis), bemaciclib (LY2835219, Lilly), 7-hydroxy staurosporine (UCN-01. Kyowa Hakko Kirin), alvocidib (flavopiridol, Sanofi), JNJ-7706621 (Johnson & Johnson), BMS-387032 (SNS-032, Bristol-Myers Squibb), AT7519M (Astex Therapeutics), riviciclib (Piramal Enterprises Ltd.), voruciclib (Piramal Enterprises Ltd.), roniciclib (BAY-1000394. Bayer), ZK-304709 (Bayer Schering Pharma), ON-123300 (Onconova), CYC-065 (Cyclacel), LS-007 (University of South Australia), PHA-793887 (Bayer), TG-02 (SB-1317, S*BIO), olomoucine or purvalanol A.

In another embodiment, the CDK inhibitor is selected from: dinaciclib, milciclib, seliciclib, alvocidib, riviciclib, voruciclib, roniciclib, 7-hydroxy staurosporine, LEE-011, bemaciclib, ZK-304709, ON-123300, LS-007 or palbociclib.

In yet another embodiment, the CDK inhibitor is selected from dinaciclib, milciclib, seliciclib, alvocidib, riviciclib, voruciclib, LEE-011, bemaciclib or palbociclib.

Dinaciclib (SCH-727965), developed by Merck & Co., is a potent and selective inhibitor of the CDK1, CDK2, CDK5 and CDK9. Dinaciclib is an experimental drug which demonstrates activity against a broad panel of tumor cell lines including breast, small cell and non-small cell lung, colon and prostate cancers. The said compound dinaciclib refers to 2-[1-[3-Ethyl-7-(1-oxidopyridin-3-ylmethylamino)pyrazolo[1,5-a]pyrimidin-5-yl]piperidin-2(S)-yl]ethanol, which is described in Published PCT Application No. WO2005077954, wherein a process for its manufacture is described.

Milciclib (PHA-848125), developed by Pfizer, is an oral multi-CDK inhibitor. The compound is currently under clinical trials for the treatment of thymic carcinoma. The said compound milciclib refers to N,1,4,4-Tetramethyl-8-[4-(4-methylpiperazin-1-yl)phenylamino]-4,5-dihydro-1H-pyrazolo[4,3-h]quinazoline-3-carboxamide, which is described in Published PCT Patent Application No. WO2004104007, wherein a process for its manufacture is described.

Seliciclib (CYC-202), developed by CNRS, is a small molecule CDK inhibitor and reported to be more potent inhibitor of CDK2. Seliciclib also known as R-roscovitine is the pure R isomer of roscovitine. The compound is currently under clinical trials for the treatment of cancers, such as lymphoma and nasopharyngeal cancer. The said compound seliciclib refers to (−)-6-(Benzylamino)-2-[1 (R)-(hydroxymethyl)propylamino]-9-isopropylpurine, which is described in Published PCT Patent Application No. WO1997020842, wherein the process for its manufacture is described.

Alvocidib (flavopiridol), developed by Sanofi (originally Hoechst Marion Roussel), is a synthetic flavonoid based on an extract from an Indian plant. Alvocidib is reported to be a pan-CDK inhibitor. Alvocidib is currently a clinical candidate for the treatment of cancers such as acute myeloid leukemia, advanced stomach cancer or gastroesophagael junction cancer, etc. The said compound alvocidib refers to (−)-cis-2-(2-Chlorophenyl)-5,7-dihydroxy-8-(3-hydroxy-1-methylpiperidin-4-yl)-4H-1-benzopyran-4-one hydrochloride, which is described in the U.S. Pat. No. 5,284,856, wherein the process for its manufacture is described.

Riviciclib, developed by Piramal Enterprises Ltd. is a potent CDK inhibitor. Riviciclib, an experimental drug for the treatment of cancer, refers to (+)-2-(2-Chlorophenyl)-5,7-dihydroxy-8-[(2R,3S)-2-(hydroxymethyl)-1-methylpyrrolidin-3-yl]-4H-chromen-4-one hydrochloride, which is described in Published PCT Patent Appln. No. WO2004004632, wherein the process for its manufacture is described.

Voruciclib, a CDK inhibitor, is developed by Piramal Enterprises Ltd. for the treatment of cancer. The said compound voruciclib refers to (+)-2-[2-Chloro-4-(trifluoromethyl)phenyl]-5,7-dihydroxy-8-[(2R,3S)-2-(hydroxymethyl)-1-methylpyrrolidin-3-yl]-4H-chromen-4-one hydrochloride, which is described in Published PCT Patent Appln. No. WO2007148158, wherein the process for its manufacture is described.

LEE-011, developed by Novartis is a CDK4, CDK6 and JAK3 inhibitor. Clinical trials for LEE-011 are ongoing for the treatment of breast cancer, solid tumors, lymphoma, melanoma, rhabdoid tumor, neuroblastoma, etc. alone or in combination with other anticancer agents. The said compound LEE-011 refers to 7-Cyclopentyl-N,N-dimethyl-2-[5-(1-piperazinyl)pyridin-2-ylamino]-7H-pyrrolo[2,3-d]pyrimidine-6-carboxamide, which is described in Published PCT Patent Appln. No. WO2007140222, wherein the process for its manufacture is described.

Bemaciclib (LY2835219), developed by Lilly, is a CDK4. CDK6 and Pim-1 kinase inhibitor. Bemaciclib is a clinical candidate for the treatment of cancer such as, relapsed or refractory mantle cell lymphoma, metastatic breast cancer, non-small cell lung cancer; either alone or in combination with other anticancer agents. The said compound bemaciclib refers to (N-[5-(4-Ethylpiperazin-1-ylmethyl)pyridin-2-yl]-5-fluoro-4-(4-fluoro-1-isopropyl-2-methyl-1H-benzimidazol-6-yl)pyrimidin-2-amine methanesulfonate, which is described in Published PCT Patent Appln. No. WO2010075074, wherein the process for its manufacture is described.

Palbociclib (PD-0332991), developed by Pfizer is a potent, highly specific, orally active small-molecule inhibitor of CDK4 and CDK6. Palbociclib is under clinical trials for the treatment of liposarcoma, breast cancer, multiple myeloma, hepatocellular carcinoma, glioblastoma multiforme, leukemia, non-small cell lung cancer, head and neck cancer, etc. The said compound palbociclib refers to 6-Acetyl-8-cyclopentyl-5-methyl-2-[5-(1-piperazinyl)pyridin-2-ylamino]pyrido[2,3-d]pyrimidin-7(8H)-one, which is described in Published PCT Patent Appln. No. WO2003062236, wherein the process for its manufacture is described.

In an embodiment, the antioxidant enzyme inhibitor is selected from thioredoxin reductase inhibitor (TrxR inhibitor), glutathione peroxidase inhibitors, glutathione reductase inhibitors, glutathione transferase inhibitors, gamma-glutamate cysteine ligase inhibitors or glutathione synthetase inhibitors.

In an embodiment, the antioxidant enzyme inhibitor is a thioredoxin reductase inhibitor (TrxR inhibitor).

In an embodiment, the antioxidant enzyme inhibitor is glutathione peroxidase inhibitor, glutathione reductase inhibitor, glutathione transferase inhibitor, gamma-glutamate cysteine ligase inhibitor or glutathione synthetase inhibitor.

In an embodiment of the present invention, the antioxidant enzyme inhibitor is a superoxide dismutase inhibitor.

In an embodiment, the antioxidant enzyme inhibitor is a NADPH oxidase inhibitor.

In an embodiment, the antioxidant enzyme inhibitor is selected from: azelaic acid (Bayer Schering), carmustine (Eisai), motexafin gadolinium (National Cancer Institute Pharmacyclics), laromustine (Nanotherapeutics Yale University), auranofin (GlaxoSmithKline), NSC-721641 (cancer Research Technology), arsenic trioxide (Cell Therapeutics), ebselen (Sanofi), aurothioglucose (Merck), cyclophosphamide (Bristol-Myers Squibb), menadione (Bristol-Myers Squibb and Sanofi), 2,4-dinitrochlorobenzene (University of California), buthionine sulfoximine (BSO, National Cancer Institute), cisplatin (Bristol-Myers Squibb), oxaliplatin (Sanofi), iniparib (University of California), ellagic acid (Sigma Chemical Aldrich), PX-C5 (ProlX), PX-12 (ProlX, Oncothyreon), PX-36 (ProlX), PX-960 (ProlX), PX-916 (ProlX). TH-169 (University of Pittsburgh), TH-223 (University of Pittsburgh), diethyldithiocarbamate, DTI-015 (Direct Therapeutics), tiomolibdic acid ammonium salt, ATN-224 (Decuprate, Tactic Pharma). CEU-025 (Universite Laval), CEU-152 (Universite Laval), CEU-169 (Universite Laval). TLK-117 (Telik), IG-1 (Jinan University), IG-3 (Jinan University), SK-053 (Polish Academy of Science). CPV-159 (Universidad de Puerto Rico). CPV-154 (Universidad de Puerto Rico), CPV-156 (Universidad de Puerto Rico), SR-4 (Beckman Research Institute City of Hope), BE-40644 (MSD) or gold complexes.

In another embodiment, the antioxidant enzyme inhibitor is TrxR inhibitor selected from azelaic acid, carmustine, motexafin gadolinium, laromustine, auranofin, NSC-721641, arsenic trioxide, ebselen, aurothioglucose, cyclophosphamide, menadione, 2,4-dinitrochlorobenzene, cisplatin, oxaliplatin, PX-C5, PX-12, PX-36, PX-960, PX-916, TH-169, TH-223, CEU-025, CEU-152, CEU-169, IG-1, IG-3, SK-053, CPV-159, CPV-154, CPV-156, BE-40644 or gold complexes.

In another embodiment, the TrxR inhibitor is selected from azelaic acid, carmustine, motexafin gadolinium, laromustine, auranofin, arsenic trioxide, ebselen, menadione, 2,4-dinitrochlorobenzene, cisplatin, oxaliplatin, aurothioglucose or gold complexes.

In another embodiment of the present invention, the antioxidant enzyme inhibitor is a glutathione peroxidase inhibitor, glutathione reductase inhibitor, glutathione transferase inhibitor, gamma-glutamate cysteine ligase inhibitor or glutathione synthetase inhibitor selected from carmustine, arsenic trioxide, buthionine sulfoximine, DTI-015, 2,4-dinitrochlorobenzene, SK-053, ellagic acid, TLK-117. SR-4 or gold complexes.

In another embodiment, the antioxidant enzyme inhibitor is a superoxide dismutase inhibitor selected from tiomolibdic acid ammonium salt, ATN-224 or diethyldithiocarbamate.

Auranofin, developed by GlaxoSmithKline, is an orally bioavailable, lipophilic, organic gold compound, having anti-inflammatory and potential antineoplastic activities and is used for the treatment of rheumatoid arthritis. Auranofin blocks the activity of thioredoxin reductase, thereby induces oxidative stress leading to the induction of apoptosis.

Arsenic trioxide, developed by Cell Therapeutics, is launched as Trisenox® for the treatment of relapsed or refractory acute promyelocytic leukemia (APL). Trisenox® has been reported to induce apoptosis by producing reactive oxygen species and mitochondrial damage in vitro and to activate caspase in vitro and in humans.

Ebselen, developed by Sanofi, is a synthetic, lipid-soluble seleno-organic compound having potent antioxidant capacity. Ebselen and ebselen diselenide have been reported as substrates for mammalian thioredoxin reductase and its reaction mechanisms have been described in *J. Biol. Chem.*, 2002, 277, 39456-62.

2,4-Dinitrochlorobenzene (DNCB), developed by University of California, is a specific inhibitor of thioredoxin reductase and could induce thioredoxin oxidation.

The CDK inhibitors and/or the antioxidant enzyme inhibitor(s) contained in the pharmaceutical combination or used in combination for the treatment of cancer, can be used in the form of their solvates, for example hydrates, and the solvates formed with other solvents of crystallization, such as alcohols, ethers, ethyl acetate, dioxane, dimethylformamide or a lower alkyl ketone, such as acetone, or mixtures thereof. The compounds contained in the pharmaceutical combination of the present invention can be used in their crystalline or amorphous forms. In general, all physical forms are suitable for the uses contemplated by the present invention and are intended to be within the scope of the present invention.

In an embodiment, in the pharmaceutical combination and/or the method of treatment of cancer and/or the use for the treatment of cancer; the CDK inhibitor is used in combination with one antioxidant enzyme inhibitor.

In an embodiment, in the pharmaceutical combination and/or the method of treatment of cancer and/or the use for the treatment of cancer, the CDK inhibitor is used in combination with two antioxidant enzyme inhibitor(s).

In an embodiment, in the pharmaceutical combination and/or the method of treatment of cancer and/or the use for the treatment of cancer; the CDK inhibitor is used in combination with one TrxR inhibitor.

In an embodiment, in the pharmaceutical combination and/or the method of treatment of cancer and/or the use for the treatment of cancer; the CDK inhibitor is used in combination with two TrxR inhibitors.

In an embodiment, in the pharmaceutical combination and/or the method of treatment of cancer and/or the use for the treatment of cancer; the CDK inhibitor is used in combination with a TrxR inhibitor and a further antioxidant enzyme inhibitor.

In an embodiment, in the pharmaceutical combination and/or the method of treatment of cancer and/or the use for the treatment of cancer; the CDK inhibitor is used in combination with a TrxR inhibitor and an antioxidant enzyme inhibitor selected from TrxR inhibitor, glutathione peroxidase inhibitors, glutathione reductase inhibitors, glutathione transferase inhibitors, gamma-glutamate cysteine ligase inhibitors or glutathione synthetase inhibitors.

In an embodiment, in the pharmaceutical combination and/or the method of treatment of cancer and/or the use for the treatment of cancer, the CDK inhibitor is used in combination with a TrxR inhibitor and the superoxide dismutase inhibitor.

In an embodiment, in the pharmaceutical combination and/or the method of treatment of cancer and/or the use for the treatment of cancer, the CDK inhibitor is used in combination with a TrxR inhibitor and a NADPH oxidase inhibitor.

In an embodiment, the CDK inhibitor is dinaciclib.

In another embodiment, the CDK inhibitor is milciclib.

In yet another embodiment, the CDK inhibitor is seliciclib.

In yet another embodiment, the CDK inhibitor is alvocidib.

In yet another embodiment, the CDK inhibitor is riviciclib.

In yet another embodiment, the CDK inhibitor is voruciclib.

In yet another embodiment, the CDK inhibitor is LEE-011.

In yet another embodiment, the CDK inhibitor is bemaciclib.

In yet another embodiment CDK inhibitor is palbociclib.

In an embodiment, the antioxidant enzyme inhibitor is azelaic acid.

In another embodiment, the antioxidant enzyme inhibitor is carmustine.

In yet another embodiment, the antioxidant enzyme inhibitor is auranofin.

In yet another embodiment, the antioxidant enzyme inhibitor is arsenic trioxide.

In yet another embodiment, the antioxidant enzyme inhibitor is ebselen.

In yet another embodiment, the antioxidant enzyme inhibitor is menadione.

In yet another embodiment, the antioxidant enzyme inhibitor is 2,4-dinitrochlorobenzene.

In yet another embodiment, the antioxidant enzyme inhibitor is cisplatin.

In yet another embodiment, the antioxidant enzyme inhibitor is oxaliplatin.

In yet another embodiment, the antioxidant enzyme inhibitor is aurothioglucose.

In yet another embodiment, the antioxidant enzyme inhibitor is diethyldithiocarbamate.

In yet another embodiment, the antioxidant enzyme inhibitor is ATN-224.

In yet another embodiment, the antioxidant enzyme inhibitor is a gold complex.

In an embodiment, the pharmaceutical combination is used in treating cancer or cancerous conditions which includes, but are not limited to, tumors of the gastrointestinal tract, breast tumors, tumors of the skin, tumors of the brain and central nervous system, tumors of the blood and lymphatic system, head and neck cancer, tumors of the excretory system, tumors of the skeletal system, tumors of the oral cavity, tumors of the respiratory tract, tumors of the reproductive system or tumors of the liver and digestive organs.

Examples of tumors of the gastrointestinal tract include, but are not limited to, colorectal, esophagus, rectum, colon, rectosigmoid junction, anus, anal canal, small intestine and stomach.

Examples of tumors of the skin include, but are not limited to, basal cell carcinoma of skin, malignant melanoma of the skin, non-melanoma skin cancer, mesothelioma, squamous cell carcinoma of skin, Kaposi's sarcoma.

Examples of tumors of the brain and central nervous system include, but are not limited to, brain, cranial nerves, spinal cord, tumors of the meninges and other parts of the central nervous system, such as glioblastomas or medulla blastomas.

Examples of tumors of the blood and lymphatic system include, but are not limited to, Hodgkin's lymphoma, non-Hodgkin's lymphoma, burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, haematopoietic and related tissues, such as diffuse large cell lymphoma. T-cell lymphoma or cutaneous T-cell lymphoma.

Examples of tumors of the excretory system include, but are not limited to, kidney, ureter, bladder, renal pelvis and other urinary organs.

Examples of tumors of the skeletal system include, but are not limited to, bone articular cartilage, bone and articular cartilage of limbs and other sites.

Examples of tumors of the oral cavity include, but are not limited to, floor of mouth, lip, tongue, gum, palate, puriform sinus, parotid gland, salivary glands, tonsil, thyroid gland, oropharynx, nasopharynx, hypopharynx, and other sites of the oral cavity.

Examples of tumors of the respiratory tract include, but are not limited to, nasal cavity, middle ear, accessory sinuses, larynx, trachea, bronchus and lung, such as small cell lung cancer and non-small cell lung cancer.

Examples of tumors of the reproductive system include, but are not limited to, cervix uteri, vulva, ovary, vagina, uterus and other sites associated with female genital organs, prostate, placenta, testis, penis, and other sites associated with male genital organs.

Examples of tumors of the liver and digestive organs include, but are not limited to, liver, intrahepatic bile ducts, gall bladder, and other parts of the biliary tract, pancreas, and other digestive organs.

In an embodiment, cancer is selected from breast tumors, tumors of the skin, head and neck cancer, tumors of the gastrointestinal tract, tumors of the respiratory tract.

In an embodiment, in the pharmaceutical combination and/or the method of treatment of cancer and/or the use for the treatment of cancer according to the present invention, the CDK inhibitor and at least one antioxidant enzyme inhibitor can be administered simultaneously.

In an embodiment, in the pharmaceutical combination and/or the method of treatment of cancer and/or the use for the treatment of cancer according to the present invention, the CDK inhibitor and at least one antioxidant enzyme inhibitor can be administered sequentially.

In an embodiment, in the pharmaceutical combination and/or the method of treatment of cancer and/or the use for the treatment of cancer according to the present invention, the CDK inhibitor can be administered prior to the administration of antioxidant enzyme inhibitor(s).

In an embodiment, in the pharmaceutical combination and/or the method of treatment of cancer and/or the use for the treatment of cancer according to the present invention, the antioxidant enzyme inhibitor(s) can be administered prior to the administration of CDK inhibitor.

In an embodiment, in the pharmaceutical combination and/or the method of treatment of cancer and/or the use for the treatment of cancer according to the present invention, the CDK inhibitor can be administered at about the same time as administration of antioxidant enzyme inhibitor(s).

In an embodiment, in the pharmaceutical combination and/or the method of treatment of cancer and/or the use for the treatment of cancer according to the present invention, the CDK inhibitor and antioxidant enzyme inhibitor(s) can be administered once a day.

In an embodiment, in the pharmaceutical combination and/or the method of treatment of cancer and/or the use for the treatment of cancer according to the present invention; the CDK inhibitor is administered once a day, while the antioxidant enzyme inhibitor(s) can be administered twice a day.

In an embodiment, in the pharmaceutical combination and/or the method of treatment of cancer and/or the use for the treatment of cancer according to the present invention; the CDK inhibitor is administered twice a day, while the antioxidant enzyme inhibitor(s) can be administered once a day.

In an embodiment, in the pharmaceutical combination and/or the method of treatment of cancer and/or the use for the treatment of cancer according to the present invention, the CDK inhibitor and antioxidant enzyme inhibitor(s) can be administered twice a day.

In an embodiment, in the pharmaceutical combination and/or the method of treatment of cancer and/or the use for the treatment of cancer according to the present invention, the CDK inhibitor and at least one TrxR inhibitor can be administered simultaneously.

In an embodiment, in the pharmaceutical combination and/or the method of treatment of cancer and/or the use for the treatment of cancer according to the present invention, the CDK inhibitor and at least one TrxR inhibitor can be administered sequentially.

In an embodiment, in the pharmaceutical combination and/or the method of treatment of cancer and/or the use for the treatment of cancer according to the present invention, the CDK inhibitor can be administered prior to the administration of TrxR inhibitor(s).

In an embodiment, in the pharmaceutical combination and/or the method of treatment of cancer and/or the use for the treatment of cancer according to the present invention, the TrxR inhibitor(s) can be administered prior to the administration of CDK inhibitor.

In an embodiment, in the pharmaceutical combination and/or the method of treatment of cancer and/or the use for the treatment of cancer according to the present invention, the CDK inhibitor can be administered at about the same time as administration of TrxR inhibitor(s).

In an embodiment, in the pharmaceutical combination and/or the method of treatment of cancer and/or the use for the treatment of cancer according to the present invention, the CDK inhibitor and TrxR inhibitor(s) can be administered once a day.

In an embodiment, in the pharmaceutical combination and/or the method of treatment of cancer and/or the use for the treatment of cancer according to the present invention; the CDK inhibitor can be administered once a day, while the TrxR inhibitor(s) can be administered twice a day.

In an embodiment, in the pharmaceutical combination and/or the method of treatment of cancer and/or the use for the treatment of cancer according to the present invention; the CDK inhibitor can be administered twice a day, while the TrxR inhibitor(s) can be administered once a day.

In an embodiment, in the pharmaceutical combination and/or the method of treatment of cancer and/or the use for the treatment of cancer according to the present invention, the CDK inhibitor and TrxR inhibitor(s) can be administered twice a day.

In an embodiment, the pharmaceutical combination and/or the method of treatment and/or the use according to the present invention can be effective for the treatment of naive and relapsed or refractory subjects suffering from cancer or cancerous conditions.

In an embodiment, the CDK inhibitor and/or one or more antioxidant enzyme inhibitor(s) can be administered by conventional routes of administration including, but not limited to oral, parenteral, nasal, rectal, sublingual, transdermal, topical, aerosol, intraocular or intratracheal.

In an embodiment, the CDK inhibitor and/or one or more of the antioxidant enzyme inhibitor(s) can be administered in a form suitable for oral administration such as tablets, lozenges, aqueous or oily suspensions, granules, powders, cachets, emulsions, capsules, syrups, elixirs and the like.

In another embodiment, the CDK inhibitor and/or one or more of the antioxidant enzyme inhibitor(s) can be administered parenterally such as, by intramuscular, intrathecal, subcutaneous, intraperitoneal, intravenous bolus injection or intravenous infusion. Parenteral administration can be accomplished by incorporating the CDK inhibitor and/or antioxidant enzyme inhibitor into a solution or suspension.

In another embodiment, the CDK inhibitor and/or one or more of the antioxidant enzyme inhibitor(s) can be administered rectally. The rectal administration includes administering the compounds into the rectum or large intestine. This can be accomplished using suppositories or enemas. Suppository formulations can be made by methods known in the art.

In one embodiment, the CDK inhibitor and/or one or more of the antioxidant enzyme inhibitor(s) can be administered in the form of a pharmaceutical composition containing the said CDK inhibitor and/or one or more of the antioxidant enzyme inhibitor(s) and at least one pharmaceutically acceptable diluent, excipient or carrier.

The pharmaceutical composition comprises a CDK inhibitor and/or at least one antioxidant enzyme inhibitor and one or more pharmaceutically acceptable diluent, excipient or carrier. For the production of pills, tablets, coated tablets and hard gelatin capsules, the pharmaceutically active excipients that can be used include, but not limited to, lactose, corn starch or derivatives thereof, gum *arabica*, magnesia or glucose, etc. For soft gelatin capsules and suppositories, the carriers that can be used include, but not limited to, fats, waxes, natural or hardened oils, etc. Suitable carriers for the production of solutions, are, for example injection solutions, or for emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned. The pharmaceutically acceptable diluents, excipients or carriers used in the pharmaceutical composition can any conventionally known pharmaceutically acceptable diluents, excipients or carriers, which can be selected depending on the dosage form and the route of administration of the CDK inhibitor and the antioxidant enzyme inhibitors.

The CDK inhibitor and/or antioxidant enzyme inhibitor can be formulated into pharmaceutical dosage forms using conventional pharmaceutical techniques familiar to one skilled in the art such as by means of blending, granulating, dissolving or lyophilizing.

In general, compositions intended for pharmaceutical use can be prepared according to any method known in the art for the manufacture of pharmaceutical compositions, e.g. *Remington—The Science and Practice of Pharmacy* (21$^{st}$ Edition) (2005), *Goodman & Gilman's The Pharmacological Basis of Therapeutics* (11th Edition) (2006) and *Ansel's Pharmaceutical Dosage Forms and Drug Delivery Systems* (9th Edition), and *Solid-State Chemistry of Drugs* (2nd Edition) (1999).

The compositions described herein can be in a form suitable for oral administration, for example, solid dosage forms such as tablets, capsules, lozenges, or granules; liquid dosage forms such as, emulsions, solutions, suspensions; for parenteral injection (including intravenous, subcutaneous, intramuscular, intravascular or infusion) for example as a sterile solution, suspension or emulsion; for topical administration for example as an ointment, cream, gel or lotion.

Compositions for oral administrations can be in the form of tablets, lozenges, aqueous or oily suspensions, granules, powders, cachets, emulsions, capsules, syrups, or elixirs. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Selectively permeable membranes surrounding an osmotically active driving compound are also suitable for oral administration of the compounds (CDK inhibitor and/or antioxidant enzyme inhibitor) contained in the pharmaceutical combination of the present invention. Compositions suitable for oral administration can include standard vehicles such as mannitol, lactose, starch, corn starch, magnesium stearate, talc, sodium saccharine, cellulose, magnesium carbonate, etc. Such vehicles are preferably of pharmaceutical grade.

For ointments and creams, the active ingredient (CDK inhibitor and/or antioxidant enzyme inhibitor) can be formulated in oil-in-water or water-in-oil base.

For intramuscular, intraperitoneal, subcutaneous and intravenous use, sterile solutions of the active ingredient (CDK inhibitor and/or antioxidant enzyme inhibitor) are usually employed, and the pH of the solutions should be suitably adjusted and buffered.

Further, the anticancer effect of the compounds (CDK inhibitor and/or antioxidant enzyme inhibitors) contained in the pharmaceutical composition can be delayed or prolonged through a proper formulation. For example, a slowly soluble pellet of the compound can be prepared and incorporated in a tablet or capsule. The technique can be improved by making pellets of several different dissolution rates and filling capsules with a mixture of the pellets. Tablets or capsules can be coated with a film which resists dissolution for a predictable period of time. Even the parenteral preparations can be made long acting, by dissolving or suspending the compound in oily or emulsified vehicles which allow it to disperse only slowly in the serum.

Although the effective doses of the CDK inhibitor and/or antioxidant enzyme inhibitor used for administration vary depending on the severity of the disease (cancer), the severity of symptoms, the age, sex, body weight and sensitivity difference of the subject (the patient), the mode, time, interval and duration of administration, the nature and type of formulation, etc. In certain embodiments, the CDK inhibitor and/or one or more antioxidant enzyme inhibitor(s) can be administered in a time frame where both the agents are still active. One skilled in the art would be able to determine such a time frame by determining the half life of the administered therapeutic agents. As indicated herein before, in the pharmaceutical combination and/or the method of treatment of cancer and/or the use for the treatment of cancer according to the present invention; the CDK inhibitor and one or more antioxidant enzyme inhibitor(s) can be administered simultaneously or sequentially and when administered sequentially in any order. The CDK inhibitor and antioxidant enzyme inhibitors can be administered in the manner that the peak pharmacokinetic effect of one compound coincides with the peak pharmacokinetic effect of the other.

In an embodiment, the CDK inhibitor and the antioxidant enzyme inhibitor can both be administered once a day. In another embodiment, the CDK inhibitor and the antioxidant enzyme inhibitor can both be administered twice a day. In a further embodiment, the CDK inhibitor can be administered once a day, while the antioxidant enzyme inhibitor(s) can be administered twice a day. In yet further embodiment, the antioxidant enzyme inhibitor can be administered once a day, while the CDK inhibitor can be administered twice a day. However, the amount of each anticancer agent when used in combination will typically be less than an amount that would produce a therapeutic effect if administered alone. For convenience, the total daily dose can be divided and administered in portions during the day, if desired.

The dosage of the therapeutic agents (CDK inhibitor and antioxidant enzyme inhibitors(s)) to be administered should be selected to produce the desired effect. A suitable dosage of the CDK inhibitor can be from about 10 mg/day to about 2000 mg/day. A suitable dosage of the antioxidant enzyme inhibitor can be from about 10 mg/day to about 3000 mg/day.

In an embodiment, the CDK inhibitor can be administered from about 50 mg/day to about 1000 mg/day. In another embodiment, the antioxidant enzyme inhibitor can be administered from about 50 mg/day to about 2000 mg/day.

The combinations provided by this invention have been evaluated in certain assay systems, and in several different administrative schedules in vitro. The experimental details are as provided herein below. The data presented herein clearly indicate that the antioxidant enzyme inhibitor, particularly a TrxR inhibitor when combined with a CDK inhibitor exhibits synergistic effect. It is clearly indicated that the therapeutic agents when used in combination in the treatment of cancer result in increasing apoptosis or cytotoxicity in proliferative cells than when the cells are treated with only the CDK inhibitor or only the antioxidant enzyme inhibitor, particularly the TrxR inhibitor.

In one aspect, the present invention relates to a pharmaceutical kit ("the kit") comprising a container containing: (i) a CDK inhibitor. (ii) one or two or more antioxidant enzyme inhibitor(s), and (iii) a package insert comprising instructions for using CDK inhibitor(s) in combination with the antioxidant enzyme inhibitor(s) for the treatment of cancer.

The kit may contain two or more separate containers for the CDK inhibitor and the antioxidant enzyme inhibitor(s). The package insert includes information about the indication, usage, doses, direction for administration, contraindications, precautions and warnings. The suitable container that can be used includes a bottle, a vial, an ampoule, a syringe or a blister pack. The pharmaceutical kit may optionally comprise a further container comprising a pharmaceutically acceptable buffer, water for injection, phosphate-buffered saline, Ringer's solution and dextrose solution.

The present invention, particularly use of the CDK inhibitor in combination with one or more antioxidant enzyme inhibitor(s) has been evaluated using certain assay methods/systems, and in several different administrative schedules in vitro and in vivo. The experimental details are as provided herein below.

Those skilled in the art will recognize that several variations are possible within the scope and spirit of this invention. The invention will now be described in greater detail by reference to the following non-limiting examples. The following examples further illustrate the invention but, of course, should not be construed as in any way limiting its scope.

The following abbreviations or terms are used herein:
- ATM: Aurothiomalate
- ATO: Arsenic trioxide
- CI: Combination index
- CDK: Cyclin-dependent kinase
- CDK inhibitor: Cyclin-dependent kinase inhibitor
- DCFDA: 2',7'-dichlorofluorescin diacetate
- DCF: 2',7'-dichlorofluorescin
- DMSO: Dimethyl sulfoxide
- DNCB: 2,4-Dinitrochlorobenzene
- DPBS: Dulbecco's Phosphate Buffered Saline
- FBS: Fetal Bovine Serum
- MCT: Micro centrifuge tube
- NADPH: Nicotinamide Adenine Dinucleotide Phosphate
- PI: Propidium iodide
- ROS: Reactive oxygen species
- TBHP: Tert-butyl hydrogen peroxide
- Trx: Thioredoxin
- TrxR: Thioredoxin reductase
- TrxR inhibitor: Thioredoxin reductase inhibitor
- Room temperature: 20-35° C.
- rpm: Revolutions per minute
- mL: Millilitre
- min: Minutes
- mg: Milligram
- nm: Nanometer
- μL: Microlitre
- μM: Micromolar
- ° C.: Degree centigrade
- h: Hour

Examples

Activity of the pharmaceutical combinations comprising CDK inhibitor and antioxidant enzyme inhibitor can be determined according to any effective in vitro or in vivo assay method.

Example 1

In-Vitro Study of the Combination of a CDK Inhibitor with a Thioredoxin Reductase Inhibitor in Different Cell Lines Objective:

The objective of this study was to evaluate the effect of the combination of voruciclib (CDK inhibitor) with thioredoxin reductase inhibitors (TrxR inhibitors) on cell growth in FaDu and MDA-MB-231 cell lines.

Protocol for CGI Assay:

Requirements:
- Cells (adherent) cell count ≥3000 cells/well.
- 96 well delta white plate (Nunc, cat #136101)
- 1×DPBS (Gibco, cat #A12856-01)
- Propidium iodide
- DMSO
- Tryphan Blue (Sigma, cat #T8154)
- Trypsin (Sigma, cat #T3924)
- FBS (Hyclone, cat #SH30071.03)

Equipment:
- Plate shaker
- −80° C. fridge
- Spectramax for reading the plates
- Incubator Protocol:

Trypsinization of Cells

The media was removed from the flask containing cells and 2-3 mL of sterile 1×DPBS was added to the flask. The DPBS was then removed from the flask and 2 mL of trypsin was added to the flask. The flask was kept in the incubator for a few seconds. The cells were then checked whether dislodged and if dislodged, 2 mL of serum was added to the flask. To the flask was then added 5-6 mL of media and swirled. The media was collected from the flask and centrifuged at 600 rpm for 10 min.

Cell Counting

The supernatant solution was decanted and the pellet was re-suspended in 10 mL of media. To a 1.7 mL MCT; 50 μL of tryphan blue, 40 μL of media and 10 μL of cell suspension were added. The solution was then vortexed and 10 μL of this solution was loaded on a hemocytometer. The cells were counted in hemocytometer chambers and further calculated to get a count of ≥3000 cells/well/200 μL.

Seeding of the Plate

The cell stock was prepared using respective media and FBS, and 200 μL of the cell stock was added to each well (except media control wells) of white delta treated 96 well plate using a multi-channel pipette. To the media control wells, 200 μL of media was added. The plates were then incubated at 37° C. for 12-16 h.

Drug Treatment

The drug (the therapeutic agent) i.e. the CDK inhibitor and the antioxidant enzyme inhibitor were separately diluted to 10 folds using DMSO. The media of the plates was changed before the addition of drug to the plates and these plates were then placed in the incubator. 1 μL of CDK inhibitor and antioxidant enzyme inhibitor was added simultaneously to the respective wells and placed on the plate shaker for 15-30 mins. The plates were then placed back in incubator for 72 h or the time of incubation as decided.

Termination

200 μL of media from each well was gently aspirated and then added 100 μL of 1×DPBS at room temperature to each well. The working stock of PI (stock 1 mg/mL) was prepared using 140 μL of PI and 20 mL of 1×DPBS for one plate. Then 1×DPBS was removed from the wells and 200 μL of PI working stock was added to each well. These plates were kept in dark for 5-10 min at room temperature on a shaker, after which the plates were stored at −80° C. until reading of the plate.

Plate Reading

The plate was read in Spectramax fluorescence excitation maximum is 535 nm and the emission maximum is 617 nm.

A] In-Vitro Study of the Combination of a CDK Inhibitor with a Thioredoxin Reductase Inhibitor in FaDu Cell Lines Materials:

Cell Lines:

The cell lines of FaDu for head and neck squamous cell carcinomas (HNSCC) obtained from ATCC (American Tissue type Culture Collection), USA were used in this study.

Method:

The analysis of combination index (CI) and cell growth inhibition was carried out using CGI assay method. The assay method is described in detailed herein above as 'protocol for CGI assay'.

The TrxR inhibitor, auranofin was used in 9 different concentrations in log 3 intervals ranging from 0.003-30 μM (i.e. at concentrations of 0.003, 0.01, 0.03, 0.1, 0.3, 1, 3, 10 and 30 μM). The TrxR inhibitors, ebselen and arsenic trioxide (ATO) were used in 8 different concentrations in log 3 intervals ranging from 0.03-100 μM (i.e. at concentrations of 0.03, 0.1, 0.3, 1, 3, 10, 30 and 100 μM). The CDK inhibitor, voruciclib was used in 8 different concentrations in log 3 intervals ranging from 0.03-100 μM.

The combination studies of CDK inhibitor with TrxR inhibitor, auranofin was carried out at 12, 24, 48 and 72 h and the time point for which optimum synergy was obtained was determined. Further, the % cell growth inhibition was studied at this time point. This method was repeated for other combinations of the CDK inhibitor with TrxR inhibitors, ebselen and ATO.

The $EC_{50}$ values of the TrxR inhibitors, ebselen and ATO were determined at 72 h and the $EC_{50}$ values of the CDK inhibitor, voruciclib and the TrxR inhibitor, auranofin were determined at 48 h.

The combination studies involved use of a fixed concentration of the CDK inhibitor (voruciclib) with varying concentrations of the TrxR inhibitor at different time points, as mentioned in the Table-1:

TABLE 1

| Sr. No. | TrxR inhibitor | Concentration of TrxR inhibitor (in log 3 intervals) | Concentration of CDK inhibitor | Hours |
|---|---|---|---|---|
| 1 | Auranofin | 0.003-30 μM | 0.1 μM | 12, 24, 48, 72 |
| 2 | Auranofin | 0.003-30 μM | 1 μM | 12, 24, 48, 72 |
| 3 | Auranofin | 0.003-30 μM | 2 μM | 12, 24, 48, 72 |
| 4 | Auranofin | 0.003-30 μM | 4 μM | 12, 24, 48, 72 |
| 5 | Ebselen | 0.03-100 μM | 0.1 μM | 72 |
| 6 | Ebselen | 0.03-100 μM | 1 μM | 72 |
| 7 | Ebselen | 0.03-100 μM | 2 μM | 72 |
| 8 | Ebselen | 0.03-100 μM | 4 μM | 72 |
| 9 | ATO | 0.03-100 μM | 0.1 μM | 72 |
| 10 | ATO | 0.03-100 μM | 1 μM | 72 |
| 11 | ATO | 0.03-100 μM | 2 μM | 72 |
| 12 | ATO | 0.03-100 μM | 4 μM | 72 |

Results:
The $EC_{50}$ values for voruciclib, auranofin, ebselen and ATO are provided in Table-2.

TABLE 2

| Drug (Therapeutic agent) | $EC_{50}$ |
|---|---|
| Voruciclib | 2.044 |
| Auranofin | 0.1501 |
| Ebselen | 4.016 |
| ATO | 4.872 |

Figure 2:
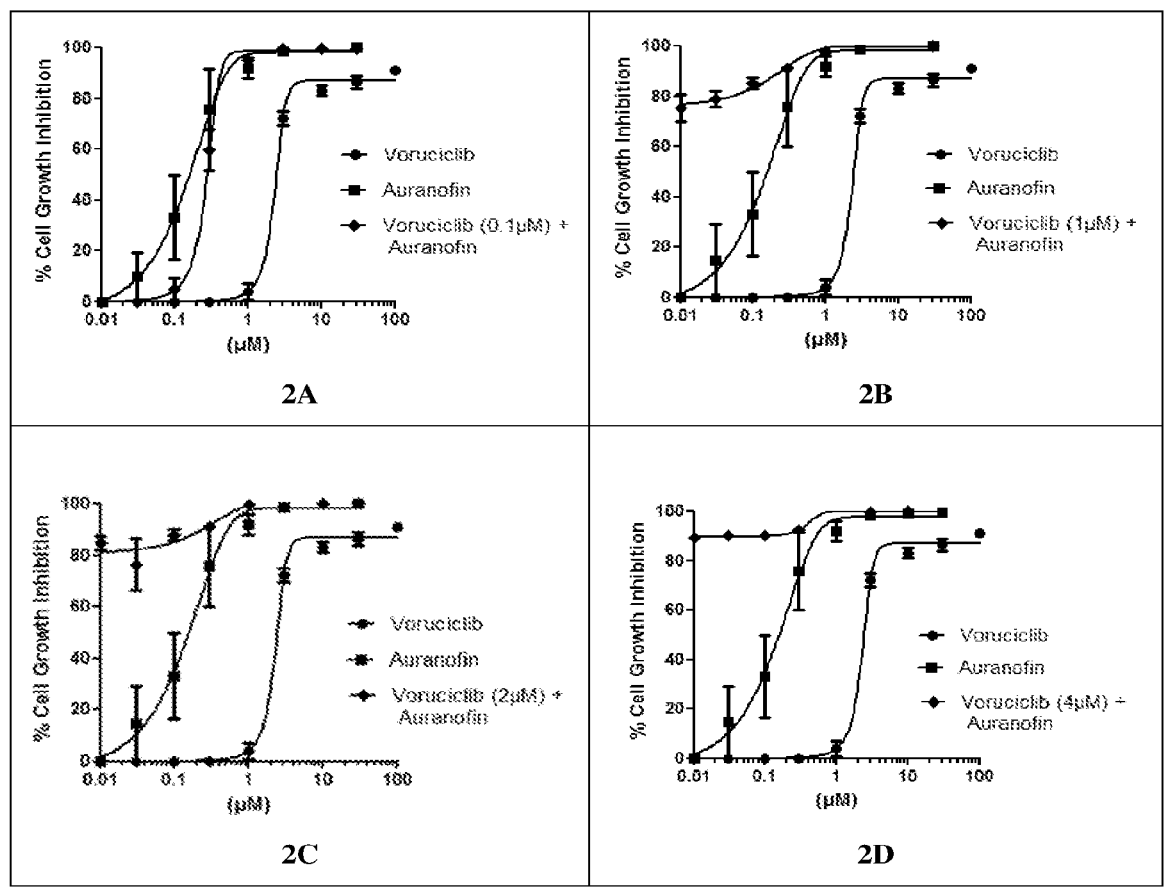
FIG. 2 depicts the effect of each of voruciclib and auranofin alone; and of the combination of voruciclib and auranofin at varying concentrations, on percentage cell growth inhibition in FaDu cell lines at 48 h.

The results of the combination studies of voruciclib and the TrxR inhibitor, auranofin at different time points of 12, 24, 48 and 72 h in FaDu cell lines are depicted as Fraction affected/combination Index plot (Fa/CI plot) in FIG. 1. The % cell growth inhibition corresponding to FIG. 1C (at 48 h) is depicted in detail in the FIG. 2 at varying concentrations of voruciclib.

Figure 3:
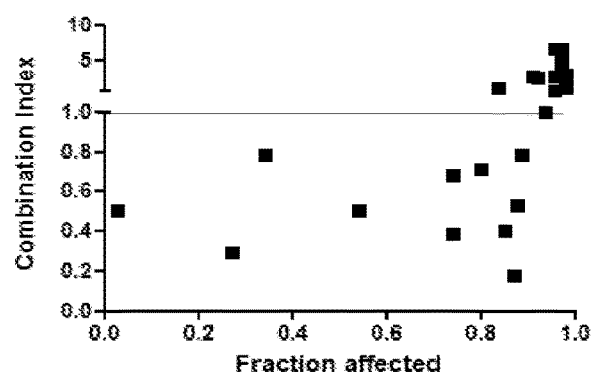
FIG. 3 depicts the effect of the combination of a CDK inhibitor such as voruciclib and an antioxidant enzyme inhibitor such as ebselen at varying concentrations in FaDu cell lines at 72 h, in terms of combination index.
Figure 4:
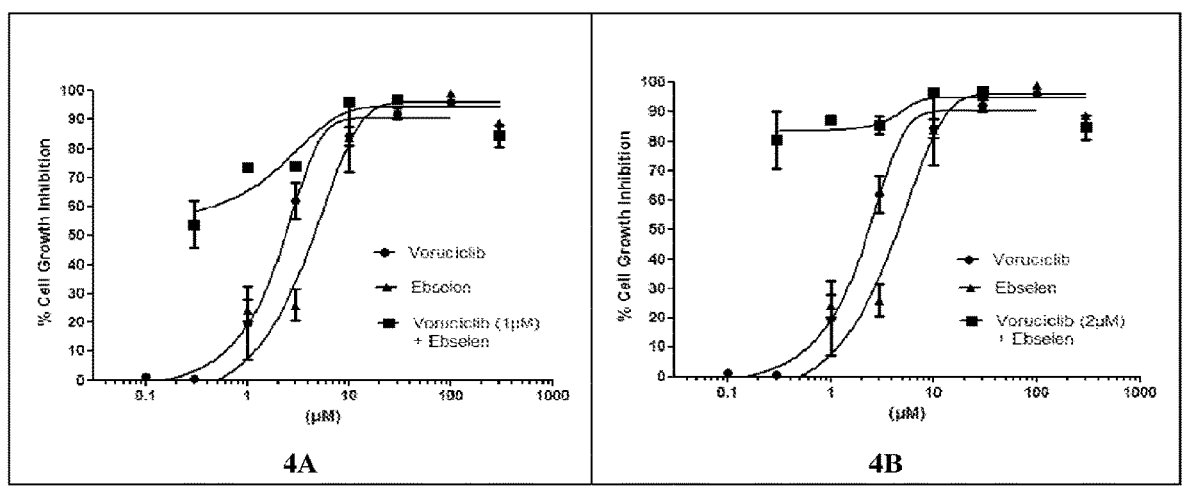
FIG. 4 depicts the effect of each of voruciclib and ebselen alone; and of the combination of voruciclib and ebselen at varying concentrations, on percentage cell growth inhibition in FaDu cell lines at 72 h.

The result of the combination studies of voruciclib and TrxR inhibitor, ebselen at 72 h in FaDu cell lines is depicted as Fa/CI plot in FIG. 3. The % cell growth inhibition corresponding to FIG. 3 is depicted in detail in the FIG. 4 at varying concentrations of voruciclib.

Figure 5:
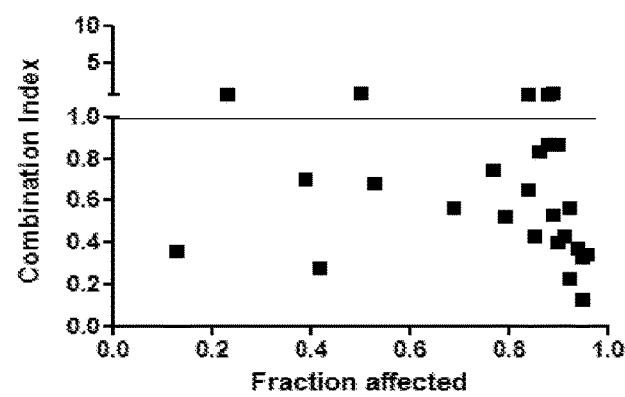
FIG. 5 depicts the effect of the combination of a CDK inhibitor such as voruciclib and an antioxidant enzyme inhibitor such as arsenic trioxide (ATO) at varying concentrations in FaDu cell lines at 72 h, in terms of combination index.
Figure 6:
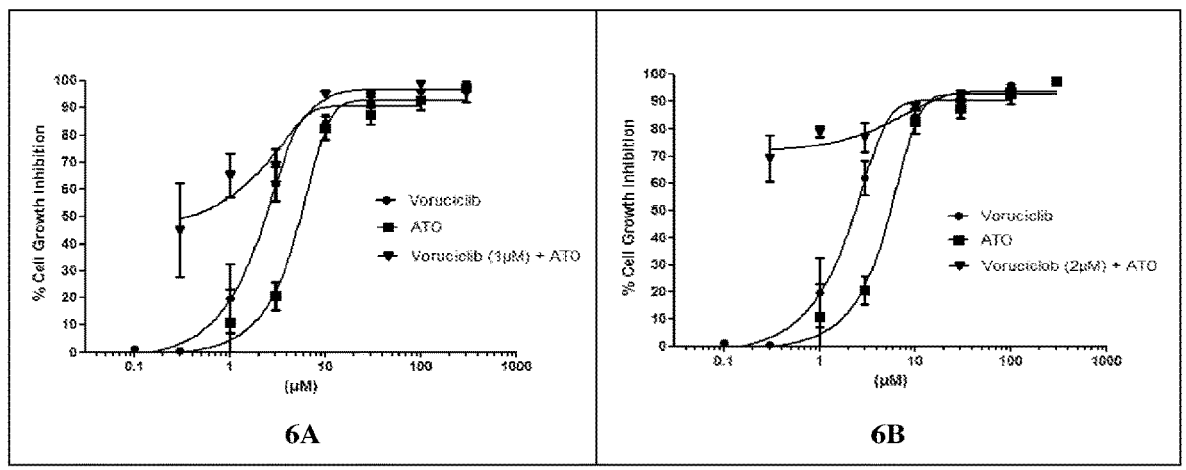
FIG. 6 depicts the effect of each of voruciclib and ATO alone; and of the combination of voruciclib and ATO at varying concentrations, on percentage cell growth inhibition in FaDu cell lines at 72 h.

The result of the combination studies of voruciclib and TrxR inhibitor, ATO at 72 h in FaDu cell lines is depicted as Fa/CI plot in FIG. 5. The % cell growth inhibition corresponding to FIG. 5 is depicted in detail in the FIG. 6 at varying concentrations of voruciclib.

Conclusion:

The combination of voruciclib and TrxR inhibitor, auranofin shows synergistic effect at different time points in FaDu cell lines with the optimum synergy being obtained at 48 h.

The combination of voruciclib and TrxR inhibitor, ebselen shows optimum synergistic effect in FaDu cell lines at 72 h.

The combination of voruciclib and TrxR inhibitor, ATO shows optimum synergistic effect in FaDu cell lines at 72 h.

B] In-Vitro Study of the Combination of a CDK Inhibitor with a Thioredoxin Reductase Inhibitor in MDA-MB-231 Cell Lines Materials:

Cell Lines:

The cell lines of MDA-MB-231 for triple negative breast cancer (TNBC) obtained from ATCC (American Tissue type Culture Collection). USA were used in this study.

Method:

The analysis of combination index and cell growth inhibition was carried out using CGI assay method. The assay method is described in detailed herein above as 'protocol for CGI assay'.

The TrxR inhibitor, auranofin was used in 9 different concentrations in log 3 intervals ranging from 0.003-30 μM (i.e. at concentrations of 0.003, 0.01, 0.03, 0.1, 0.3, 1, 3, 10 and 30 μM). The TrxR inhibitors, ebselen and ATO were used in 8 different concentrations in log 3 intervals ranging from 0.03-100 μM (i.e. at concentrations of 0.03, 0.1, 0.3, 1, 3, 10, 30 and 100 μM). The CDK inhibitor, voruciclib was used in 8 different concentrations in log 3 intervals ranging from 0.03-100 μM.

The combination studies of CDK inhibitor with each of the TrxR inhibitors, auranofin, ebselen and ATO was carried out at 12, 24, 48 and 72 h and the time point for which optimum synergy was obtained was determined. Further, the % cell growth inhibition was studied at this time point.

The $EC_{50}$ values of the CDK inhibitor, voruciclib and TrxR inhibitors, auranofin, ebselen and ATO were determined at 72 h.

The combination studies involved use of a fixed concentration of the CDK inhibitor (voruciclib) with varying concentrations of the TrxR inhibitor, as mentioned in the Table-3:

TABLE 3

| Sr. No. | TrxR inhibitor | Concentration of TrxR inhibitor (in log 3 intervals) | Concentration of CDK inhibitor | Hours |
|---|---|---|---|---|
| 1 | Auranofin | 0.003-30 μM | 0.1 μM | 72 |
| 2 | Auranofin | 0.003-30 μM | 1 μM | 72 |
| 3 | Auranofin | 0.003-30 μM | 2 μM | 72 |
| 4 | Auranofin | 0.003-30 μM | 4 μM | 72 |
| 5 | Ebselen | 0.03-100 μM | 0.1 μM | 72 |
| 6 | Ebselen | 0.03-100 μM | 1 μM | 72 |
| 7 | Ebselen | 0.03-100 μM | 2 μM | 72 |
| 8 | Ebselen | 0.03-100 μM | 4 μM | 72 |
| 9 | ATO | 0.03-100 μM | 0.1 μM | 72 |
| 10 | ATO | 0.03-100 μM | 1 μM | 72 |
| 11 | ATO | 0.03-100 μM | 2 μM | 72 |
| 12 | ATO | 0.03-100 μM | 4 μM | 72 |

Results:

The EC$_{50}$ values for voruciclib, auranofin, ebselen and ATO are provided in Table-4.

TABLE 4

| Drug (Therapeutic agent) | EC$_{50}$ |
|---|---|
| Voruciclib | 2.3 |
| Auranofin | 0.1501 |
| Ebselen | 3.891 |
| ATO | 5.189 |

Figure 7:
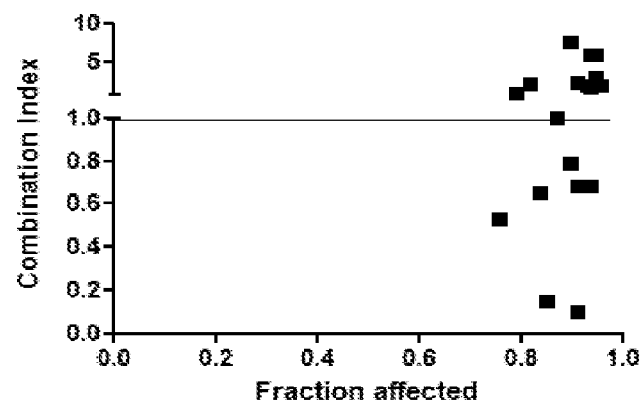
FIG. 7 depicts the effect of the combination of voruciclib and auranofin at varying concentrations in MDA-MB-231 cell lines at 72 h, in terms of combination index.
Figure 8:
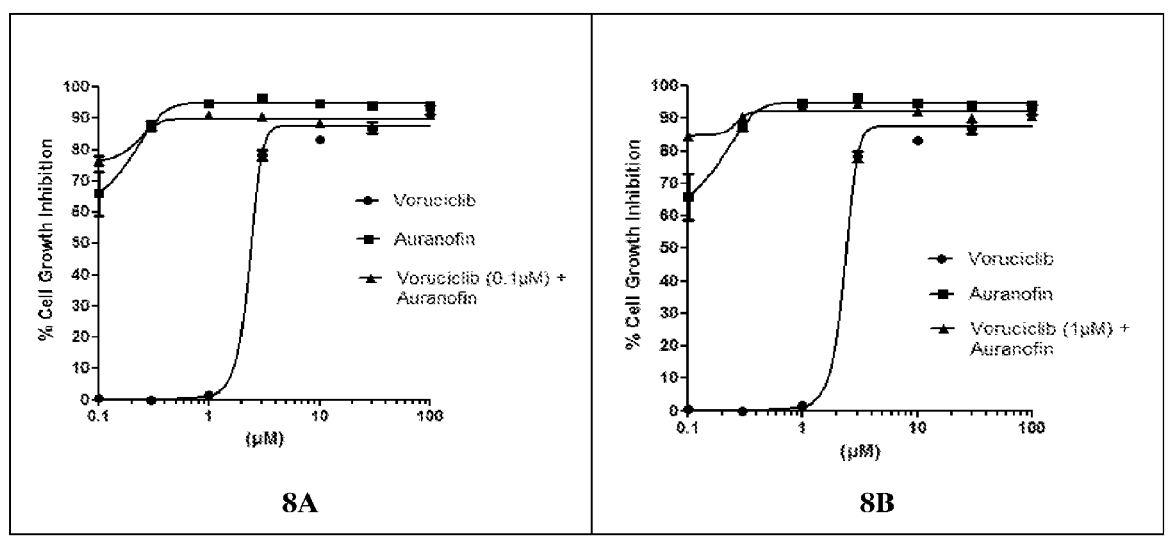
FIG. 8 depicts the effect of each of voruciclib and auranofin alone; and of the combination of voruciclib and auranofin at varying concentrations, on percentage cell growth inhibition in MDA-MB-231 cell lines at 72 h.

The result of the combination studies of voruciclib and TrxR inhibitor, auranofin at 72 h in MDA-MB-231 cell lines is depicted as Fa/CI plot in FIG. 7. The % cell growth inhibition corresponding to FIG. 7 is depicted in detail the in FIG. 8 at varying concentrations of voruciclib.

Figure 9:
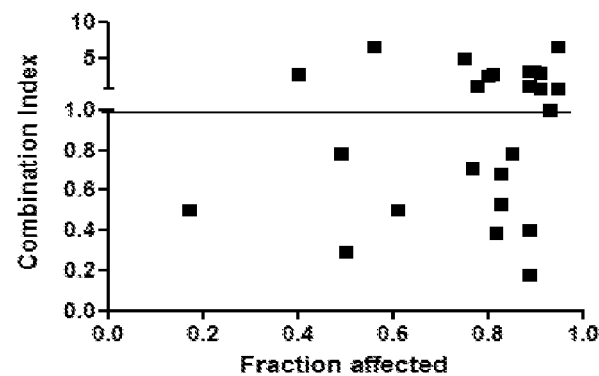
FIG. 9 depicts the effect of the combination of voruciclib and ebselen at varying concentrations in MDA-MB-231 cell lines at 72 h, in terms of combination index.
Figure 10:
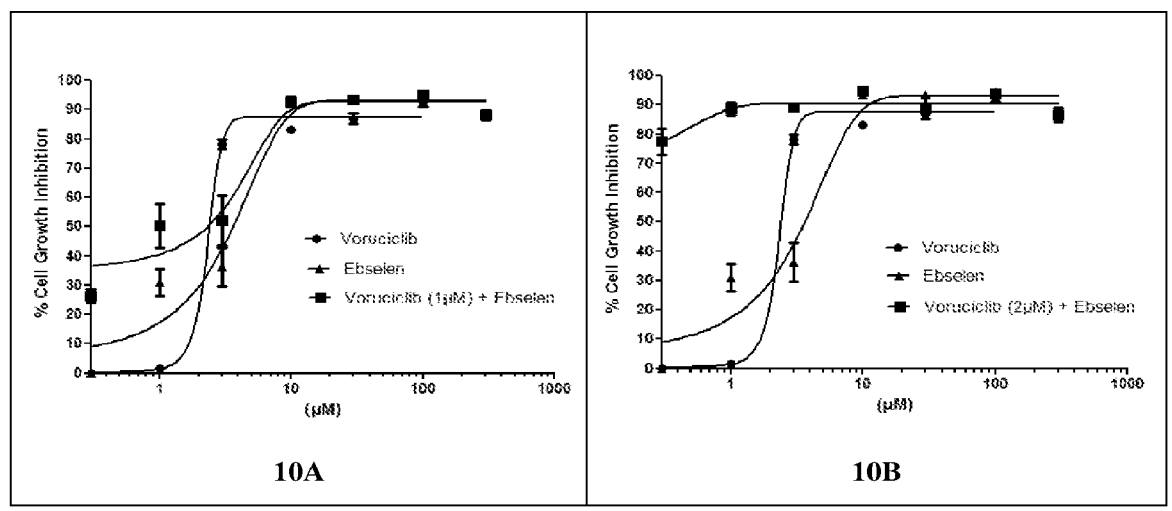
FIG. 10 depicts the effect of each of voruciclib and ebselen alone; and of the combination of voruciclib and ebselen at varying concentrations, on percentage cell growth inhibition in MDA-MB-231 cell lines at 72 h.

The result of the combination studies of voruciclib and TrxR inhibitor, ebselen at 72 h in MDA-MB-231 cell lines is depicted as Fa/CI plot in FIG. 9. The % cell growth inhibition corresponding to FIG. 9 is depicted in detail in the FIG. 10 at varying concentrations of voruciclib.

Figure 11:
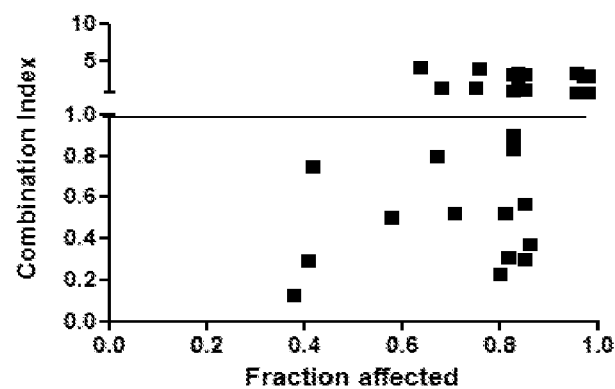
FIG. 11 depicts the effect of the combination of voruciclib and ATO at varying concentrations in MDA-MB-231 cell lines at 72 h, in terms of combination index.
Figure 12:
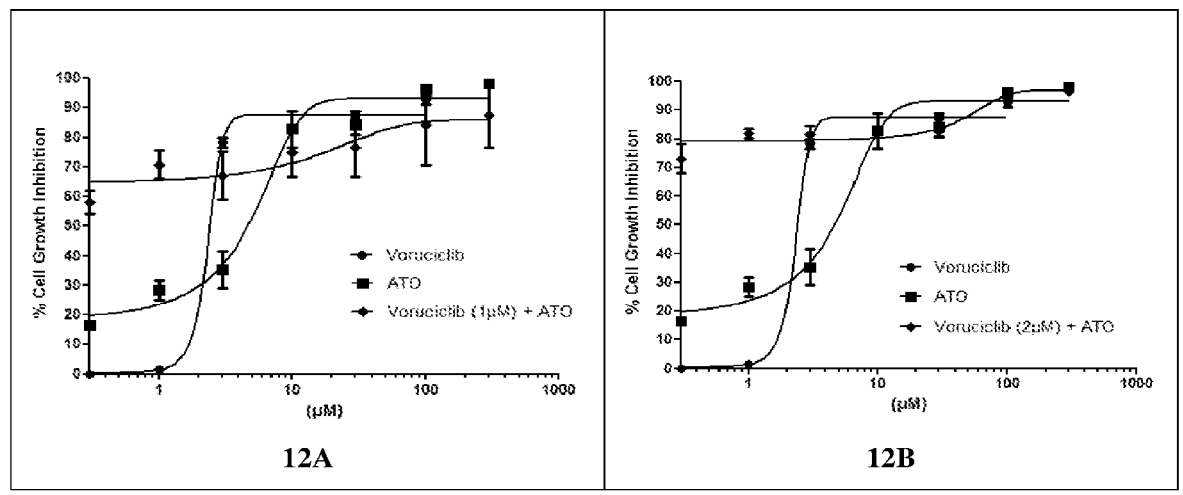
FIG. 12 depicts the effect of each of voruciclib and ATO alone; and of the combination of voruciclib and ATO at varying concentrations, on percentage cell growth inhibition in MDA-MB-231 cell lines at 72 h.
Figure 13A:
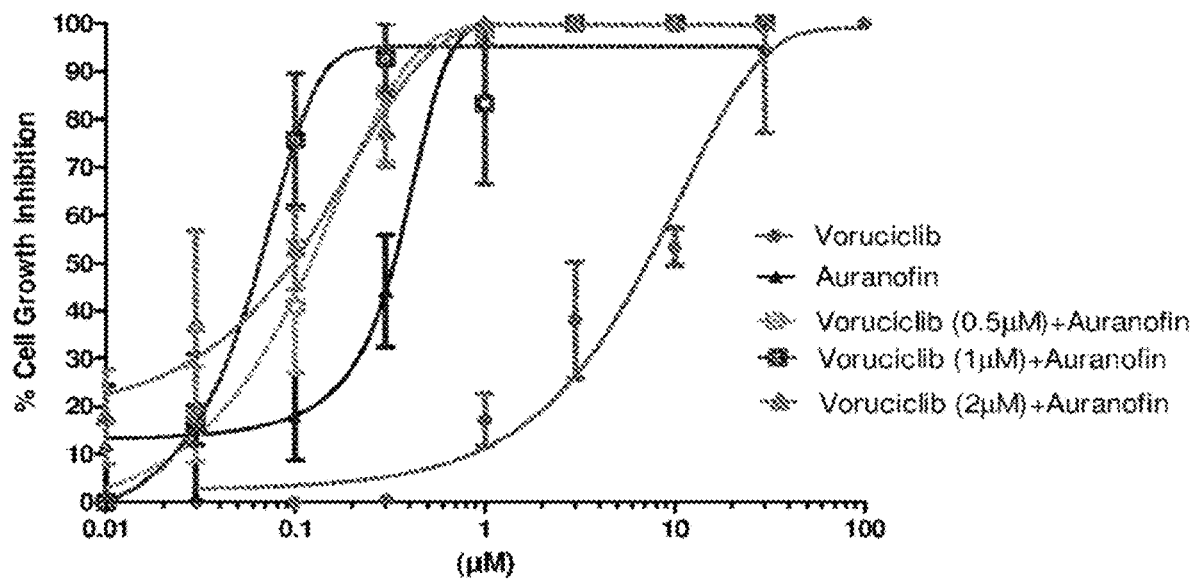
FIG. 13 depicts the effect of combination of voruciclib and TrxR inhibitor on cell growth assay in hPBMC cells after either 72 hours treatment by ATO/ebselen or 48 hours with auranofin.
Figure 13B:
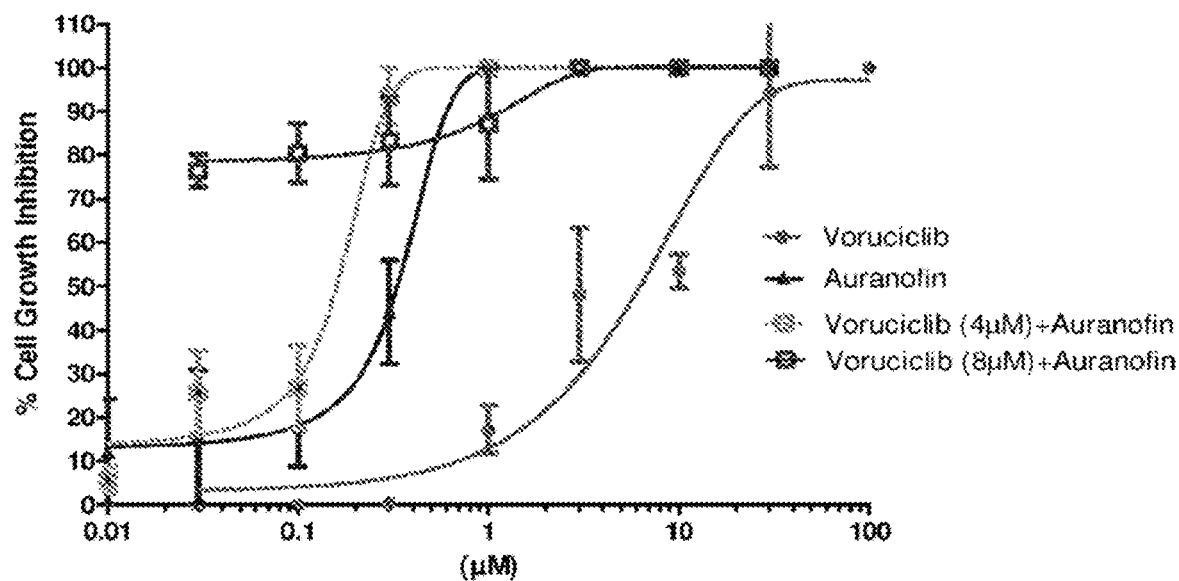
Figure 13C:
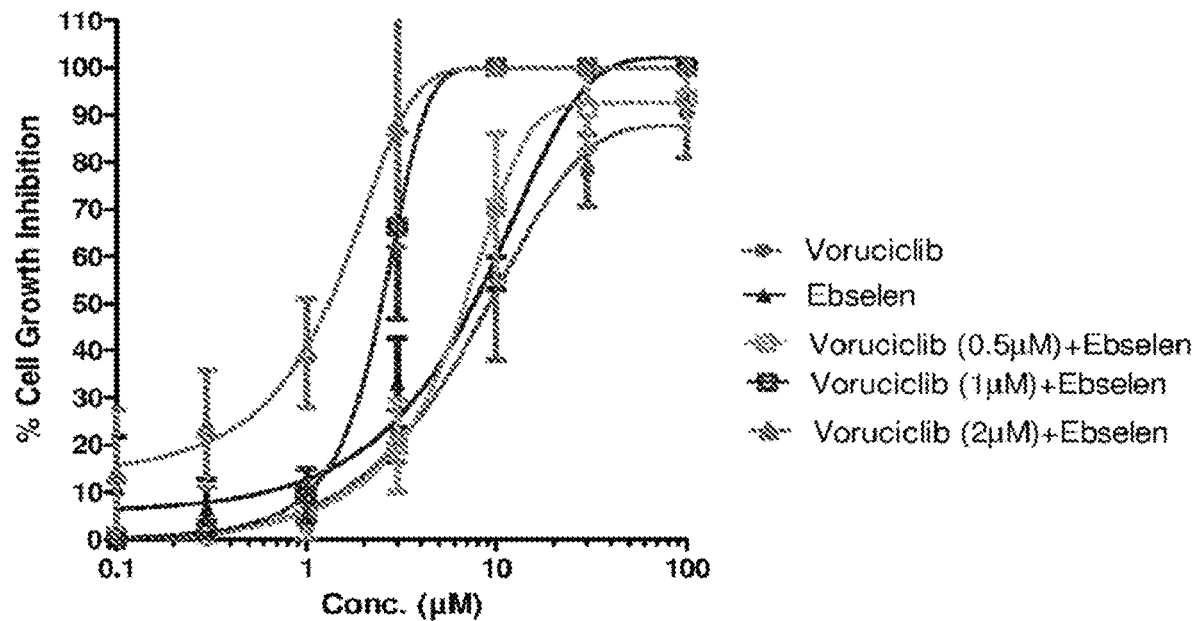
Figure 13D:
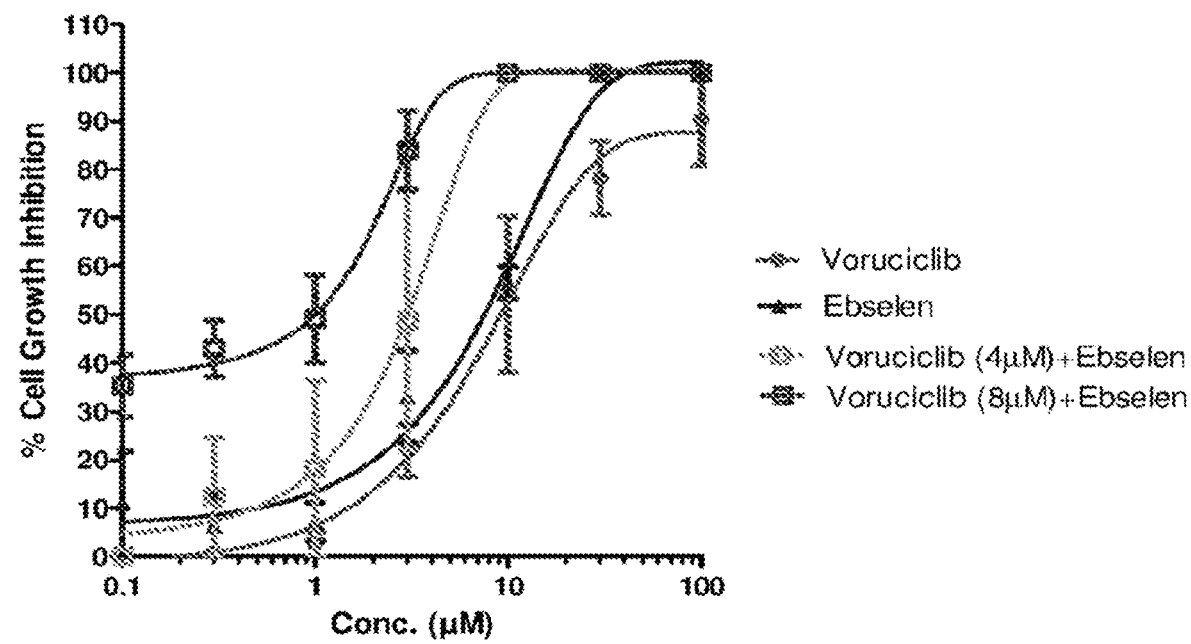

The result of the combination studies of voruciclib and TrxR inhibitor, ATO at 72 h in MDA-MB-231 cell lines is depicted as Fa/CI plot in FIG. 11. The % cell growth inhibition corresponding to FIG. 11 is depicted in detail in the FIG. 12 at varying concentrations of voruciclib.

Conclusion:

The combination of voruciclib and TrxR inhibitor, auranofin shows optimum synergistic effect in MDA-MB-231 cell lines at 72 h.

The combination of voruciclib and TrxR inhibitor, ebselen shows optimum synergistic effect in MDA-MB-231 cell lines at 72 h.

The combination of voruciclib and TrxR inhibitor, ATO shows optimum synergistic effect in MDA-MB-231 cell lines at 72 h.

Example 2

In-Vitro Study of the Combination of a CDK Inhibitor with a Thioredoxin Reductase Inhibitor on Cell Growth and Cytotoxicity in Normal Cells Objective:

The objective of this study was to evaluate the effect of the combination of voruciclib (CDK inhibitor) with thioredoxin reductase inhibitors (TrxR inhibitors) on hPBMC and MRC5 cells.

A) In-Vitro Study of the Combination of a CDK Inhibitor with a Thioredoxin Reductase Inhibitor on Cell Growth and Cytotoxicity in hPBMC Cells Materials:

Cells:

The hPBMC (human peripheral blood mononuclear cells) were used in this study.

Method:

The analysis of cell growth inhibition was carried out using CGI assay method. The assay method is described in detail in Example 1 as 'protocol for CGI assay'.

The TrxR inhibitor, auranofin was used in 8 different concentrations in log 3 intervals ranging from 0.003-30 µM (i.e. at concentrations of 0.003, 0.01, 0.03, 0.1, 0.3, 1, 3, 10 and 30 µM). The TrxR inhibitors, ebselen and ATO were used in 8 different concentrations in log 3 intervals ranging from 0.03-100 µM (i.e. at concentrations of 0.03, 0.1, 0.3, 1, 3, 10, 30 and 100 µM).

The combination studies were carried out with fixed concentration of CDK inhibitor with varying concentrations of the TrxR inhibitors, auranofin, ebselen and ATO. The study was performed at 6 to 8 different concentrations of CDK inhibitor, voruciclib in intervals ranging from 0.5-20 µM (i.e. at concentrations of 0.5.1, 2, 4, 8, 10 and 20 µM) for either 72 h ebselen and ATO or 48 h auranofin.

Results:

The result of the combination studies of voruciclib and TrxR inhibitor, auranofin at 48 h or ebselen at 72 h in hPBMC cells is depicted in FIGS. 13A, 13B, 13C and 13D respectively. The % cell growth inhibition in hPBMC cells is depicted in the figures at varying concentrations of auranofin or ebselen.

Conclusion:

The combination study shows that auranofin or ebselen at lower concentrations require >8 µM of voruciclib to start showing significant cell growth inhibition in hPBMC cells.

B) In-Vitro Study of the Combination of a CDK Inhibitor with a Thioredoxin Reductase Inhibitor on Cell Growth and Cytotoxicity in MRC5 Cells Materials:

Cells:

The MRC5 (human normal lung fibroblast cells) were used in this study.

Method:

The analysis of cell growth inhibition was carried out using CGI assay method. The assay method is described in detailed in Example 1 as 'protocol for CGI assay'.

The TrxR inhibitor, auranofin was used in 8 different concentrations in log 3 intervals ranging from 0.003-30 µM (i.e. at concentrations of 0.01, 0.03, 0.1, 0.3, 1, 3, 10 and 30 µM). The TrxR inhibitors, ebselen and ATO were used in 8 different concentrations in log 3 intervals ranging from 0.03-100 µM (i.e. at concentrations of 0.03, 0.1, 0.3, 1, 3, 10, 30 and 100 µM).

The combination studies were carried out with fixed concentration of CDK inhibitor with varying concentrations of the TrxR inhibitors, auranofin, ebselen and ATO. The study was performed at 6 to 8 different concentrations of CDK inhibitor, voruciclib in intervals ranging from 0.5-20 µM (i.e. at concentrations of 0.5, 1, 2, 4, 8, 10 and 20 µM) for either 72 h ebselen and ATO; or 48 h auranofin.

Figure 14:
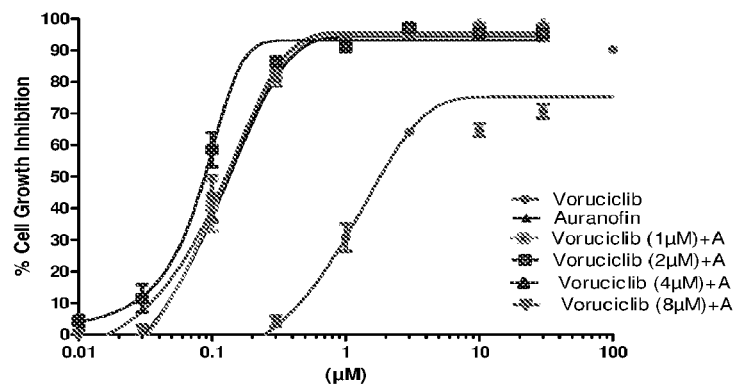
FIG. 14 depicts the effect of combination of voruciclib and TrxR inhibitor on cell growth assay in MRC5 cells after either 72 hours treatment by ATO/ebselen or 48 hours with auranofin.
Figure 14:
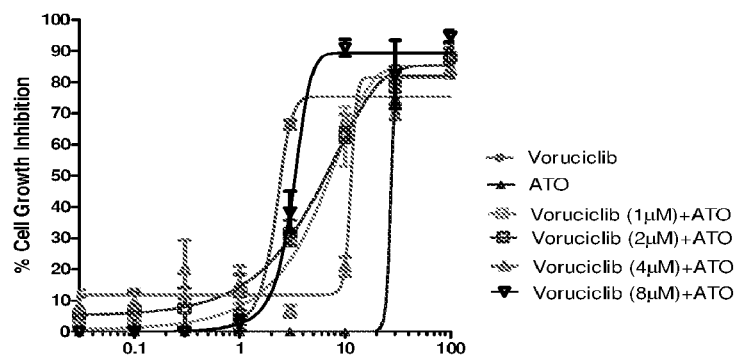
Figure 14:
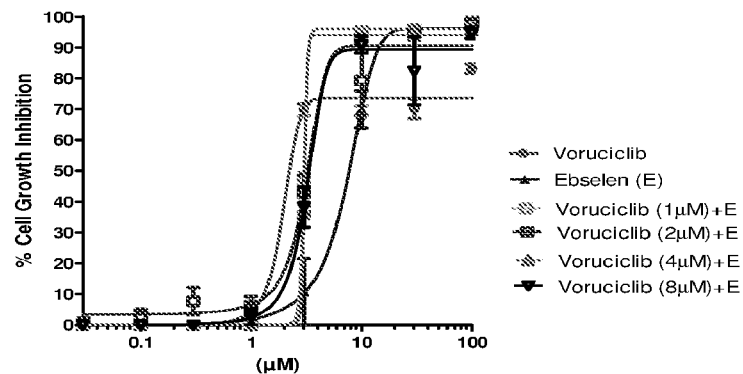

Results:

The result of the combination studies of voruciclib and TrxR inhibitor, auranofin at 48 h or ebselen and ATO at 72 h in MRC5 cells is depicted in FIGS. 14A, 14B and 14C respectively. The % cell growth inhibition in MRC5 cells is depicted in the figures at varying concentrations of auranofin/ebselen/ATO.

Conclusion:

The study shows that there is no synergistic effect in cell growth inhibition of MRC5 cells when given in combination with voruciclib and TrxR inhibitor, auranofin/ebselen/ATO over single dose of voruciclib alone.

Example 3

In-Vitro Study of the Combination of a CDK Inhibitor with a Thioredoxin Reductase Inhibitor, Auranofin on ROS Production in Cancer Cells Objective:

The objective of this study was to evaluate the effect of the combination of voruciclib with thioredoxin reductase inhibitors, auranofin on ROS production in cancer cells.

Protocol for Cellular Reactive Oxygen Species (ROS) Detection Assay Using DCFDA:

Requirements:
  Cells (adherent) cell count ≥25000 cells/well.
  DCFDA—Cellular Reactive Oxygen Species Detection Assay Kit (ab113851)
  Drug dilutions.
  96 well optical bottom polymer base black (Nunc cat #165305)
  1×DPBS (Gibco cat #A12856-01)
  Tryphan Blue. (Sigma cat #T8154)
  Trypsin (Sigma cat #T3924)
  FBS (Hyclone cat #SH30071.03)
  Respective Media.
  Aluminum foil.

Equipment:
  Plate shaker.
  −80° C. fridge.
  Fluorescence plate reader.
  Incubator.

Protocol:

Trypsinization of Cells

The media was removed from the flask containing cells and 2-3 mL of sterile 1×DPBS was added to the flask. The DPBS was then removed from the flask and 2 mL of trypsin was added to the flask. The flask was kept in the incubator for a few seconds. The cells were then checked whether dislodged and if dislodged, 2 mL of serum was added to the flask. To the flask was then added 5-6 mL of media and swirled. The media was collected from the flask and centrifuged at 600 rpm for 10 min.

Cell Counting

The supernatant solution was decanted and the pellet was re-suspended in 10 mL of media. To a 1.7 mL MCT; 50 μL of tryphan blue, 40 μL of media and 10 μL of cell suspension were added. The solution was then vortexed and 10 μL of this solution was loaded on a hemocytometer. The cells were counted in hemocytometer chambers and further calculated to get a count of ≥25000 cells/well/200 μL.

Seeding of the Plate

The cell stock was prepared using respective media and FBS, and 200 μL of the cell stock was added to each well (except media control wells) of black polymer base 96 well plate using a multi-channel pipette. To the media control wells, 200 μL of media was added. The plates were then incubated at 37° C. for 12-16 h.

Drug Treatment and Termination

The drug (the therapeutic agent) i.e. the CDK inhibitor and the antioxidant enzyme inhibitor were separately diluted to 10 folds using DMSO. The media of the plates was removed and 100 μL/well of 1× Buffer was added. The 1× Buffer and stain cells were removed by addition of 100 UL/well of diluted DCFDA solution. The plates were kept in the dark in a incubator for 45 mins at 37° C. The DCFDA solution was removed and 100 μL/well of 1× Buffer or 1×PBS was added. 1 μL of CDK inhibitor and antioxidant enzyme inhibitor was added simultaneously to the respective wells and placed on the plate shaker for few mins. The plates were then placed back in incubator for 6 h.

Plate Reading

The plate was read in Spectramax fluorescence excitation maximum is 485 nm and the emission maximum is 535 nm.

Materials:
(i) Cell lines: The cell lines of FaDu for head and neck squamous cell carcinomas (HNSCC) obtained from ATCC (American Tissue type Culture Collection), USA. The cell lines of MDA-MB-231 for triple negative breast cancer (TNBC) obtained from ATCC (American Tissue type Culture Collection). USA.
(ii) 2',7'-dichlorofluorescin diacetate (DCFDA), a fluorogenic dye that measures hydroxyl, peroxyl and other reactive oxygen species (ROS) levels within the cell.

Method:

The analysis of ROS production was carried out using DCFDA assay method. The assay method is described in detailed herein above as 'protocol for Cellular Reactive Oxygen Species (ROS) Detection Assay using DCFDA'.

The FaDu/MDAMB-431 cells were treated with various concentrations (μM) of auranofin or voruciclib alone or in combination. The cell were then cultured for 3 to 4 h and labeled with 20 μM DCFDA. The treated FaDu/MDAMB-431 cells were analyzed on a fluorescent plate reader vis-a-vis the cells of positive control which were treated with 50 μM tert-butyl hydrogen peroxide (TBHP).

Figure 15:
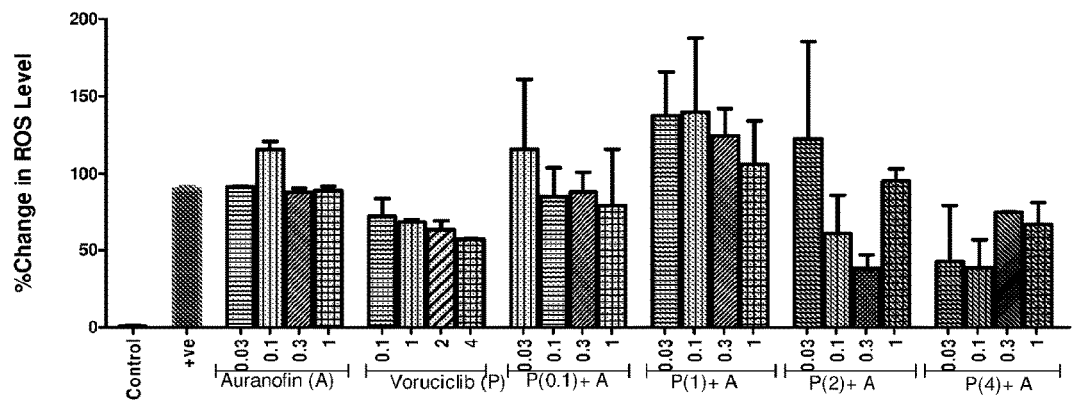
FIG. 15 depicts the effect on ROS production after treatment with auranofin and voruciclib alone or in combination in FaDu cells.

Results:

The effect of ROS production after treatment with auranofin and voruciclib alone or in combination in FaDu cells are depicted in FIG. 15. The data is represented as mean+SEM (N=2) of % change in ROS level (Y-axis) against various concentrations (μM) of auranofin or voruciclib or combination of both (X-axis), +ve: Positive control; cells treated with 50 μM tert-butyl hydrogen peroxide (TBHP). Control: Vehicle control, A: Auranofin, P: voruciclib.

Conclusion:

The study clearly indicated that there was a significant increase in ROS level i.e. ~100% by single agent auranofin and ~80% by voruciclib respectively as compared to untreated control. Also, a further increase in ROS level was found in combination treatment wherein the concentration of voruciclib was 0.1 and 1.0 μM.

Example 4

In Vitro Study on the Effect of Voruciclib in Combination with TrxR Inhibitors on TrxR Activity in Cancer Cells Objective:

The objective of this study was to determine the involvement of TrxR in both treated and untreated FaDu cells (auranofin or voruciclib as single agent or in combination) which can provide insight into the mechanism of action of combination.

Materials:
(i) Cell lines: The cell lines of FaDu for head and neck squamous cell carcinomas (HNSCC) obtained from ATCC (American Tissue type Culture Collection). USA.
(ii) DTNB: Dithio nitro benzoic acid
(iii) ATM: Aurothiomalate Method:

TrxR assay was conducted in six-well plates with IM cells per well. The cells were treated with various concentrations of auranofin or voruciclib and in combination of both. The TrxR activity was measured in cell lysates using DTNB (Dithio nitro benzoic acid). The DTNB was reduced to TNB (Thio nito benzoic acid) with or without a specific TrxR inhibitor, Aurothiomalate (ATM). The TrxR activity was calculated based on the difference in slope obtained from linear kinetic of DTNB reduction with or without ATM treatment.

Figure 16:
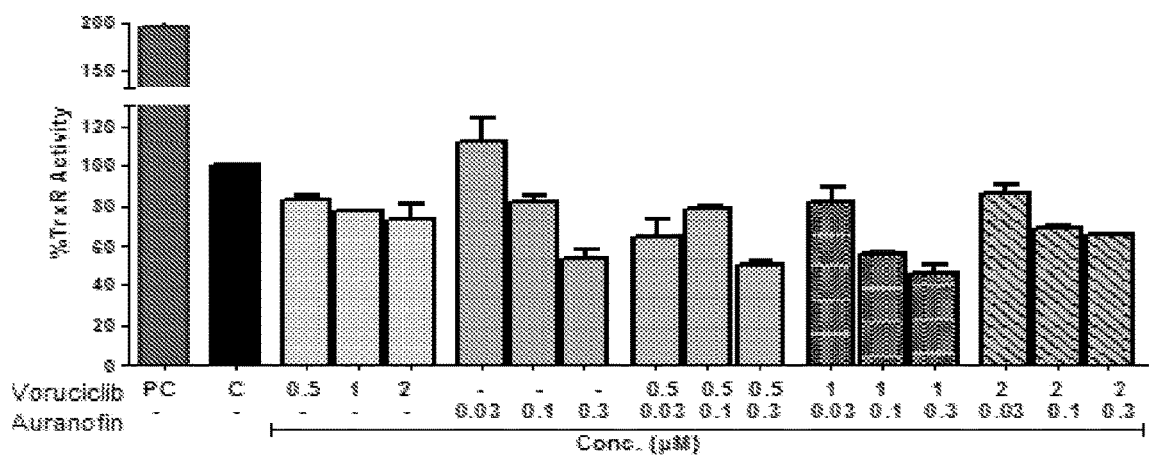
FIG. 16 depicts the effect of combination of auranofin and voruciclib on Thioredoxin Reductase (TrxR) Assay in FaDu cells.

Results:

The effect of auranofin and voruciclib combination on TrxR activity assay in FaDu cells are depicted in FIG. 16. The data is represented as mean±SEM (N=2) of % TrxR activity (Y-axis) and various concentration (μM) of Auranofin or voruciclib or combination of both (X-axis); PC-Positive control, C-Vehicle control.

Conclusion:

The study showed that there was a concentration dependent reduction in TrxR activity when cells were treated with auranofin. Further, the study revealed that there was no effect of voruciclib on TrxR activity either as a single agent or when combined with auranofin.

We claim:

1. A pharmaceutical combination comprising voruciclib and at least one antioxidant enzyme inhibitor, for use in the treatment of a cancer selected from head and neck cancer, lung cancer, gastrointestinal cancer, blood and/or lymphatic system cancer, and breast cancer.

2. The pharmaceutical combination according to claim 1, wherein the antioxidant enzyme inhibitor is selected from a glutathione peroxidase inhibitor, glutathione reductase inhibitor, glutathione transferase inhibitor, gamma-glutamate cysteine ligase inhibitor, glutathione synthetase inhibitor, thioredoxin reductase inhibitor, NADPH oxidase inhibitor, catalase inhibitor, peroxiredoxin inhibitor or superoxide dismutase inhibitor.

3. The pharmaceutical combination according to claim 2, comprising a cyclin-dependent kinase (CDK) inhibitor, a TrxR inhibitor and a further antioxidant enzyme inhibitor.

4. The pharmaceutical combination according to claim 1, wherein the at least one antioxidant enzyme inhibitor is one antioxidant enzyme inhibitor.

5. The pharmaceutical combination according to claim 1, wherein the at least one antioxidant enzyme inhibitor is two antioxidant enzyme inhibitors.

6. The pharmaceutical combination according to claim 1, further comprising an additional cyclin-dependent kinase (CDK) inhibitor selected from palbociclib, dinaciclib, seliciclib, milciclib, LEE-011, bemaciclib, 7-hydroxy staurosporine, alvocidib, JNJ-7706621, BMS-387032, AT7519M, riviciclib, roniciclib, ZK-304709, ON-123300, CYC-065, LS-007, PHA-793887, TG-02, olomoucine or purvalanol A.

7. The pharmaceutical combination according to claim 1, wherein the cancer is head and neck cancer.

8. The pharmaceutical combination according to claim 1, wherein the cancer is breast cancer.

9. The pharmaceutical combination according to claim 1, wherein the cancer is blood or lymphatic system cancer.

10. The pharmaceutical combination according to claim 1, wherein the cancer is lung cancer.

11. The pharmaceutical combination according to claim 1, wherein the cancer is gastrointestinal cancer.

12. The pharmaceutical combination according to claim 1, wherein voruciclib comprises (+)-trans-2-(2-chloro-4-trifluoromethylphenyl)-5,7-dihydroxy-8-(2-hydroxymethyl-1-methyl-pyrrolidin-3-yl)-chromen-4-one, or a salt thereof.

13. The pharmaceutical combination according to claim 1, wherein voruciclib comprises (+)-trans-2-(2-chloro-4-trifluoromethylphenyl)-5,7-dihydroxy-8-(2-hydroxymethyl-1-methyl-p yrrolidin-3-yl)-chromen-4-one hydrochloride.

14. The pharmaceutical combination according to claim 1, wherein the at least one antioxidant enzyme inhibitor comprises at least one thioredoxin reductase inhibitor (TrxR inhibitor).

15. The pharmaceutical combination according to claim 14, wherein the at least one thioredoxin reductase inhibitor is auranofin.

16. The pharmaceutical combination according to claim 14, wherein the at least one thioredoxin reductase inhibitor is ebselen.

17. The pharmaceutical combination according to claim 14, wherein the at least one thioredoxin reductase inhibitor is arsenic trioxide.

* * * * *